United States Patent
Kuwana et al.

(10) Patent No.: US 7,795,018 B2
(45) Date of Patent: Sep. 14, 2010

(54) MONOCYTE-ORIGIN MULTIPOTENT CELL MOMC

(75) Inventors: Masataka Kuwana, Tokyo (JP); Hiroaki Kodama, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 10/549,707

(22) PCT Filed: Mar. 18, 2004

(86) PCT No.: PCT/JP2004/003680

§ 371 (c)(1), (2), (4) Date: Oct. 27, 2005

(87) PCT Pub. No.: WO2004/083414

PCT Pub. Date: Sep. 30, 2004

(65) Prior Publication Data

US 2006/0171928 A1    Aug. 3, 2006

(30) Foreign Application Priority Data

Mar. 18, 2003 (JP) ............... 2003-074573

(51) Int. Cl.
C12N 5/077 (2010.01)
C12N 5/0786 (2010.01)
C12N 5/0789 (2010.01)
C12N 5/0793 (2010.01)
G01N 33/00 (2006.01)
G01N 33/53 (2006.01)

(52) U.S. Cl. .............. 435/325; 435/343; 435/7.24; 435/373; 435/377; 435/7.1

(58) Field of Classification Search ............ None
See application file for complete search history.

(56) References Cited

U.S. PATENT DOCUMENTS

2002/0164794 A1* 11/2002 Wernet .................. 435/372
2002/0182188 A1* 12/2002 Reid et al. ............. 424/93.21

FOREIGN PATENT DOCUMENTS

WO    WO 2004/043990 A2    5/2004
WO    WO 2004/043990 A3    5/2004

OTHER PUBLICATIONS

Kuwana et al., Jour Leukocyte Biol 74: 833-845, 2003.*
Stem Cells NIH, Jun. 2001, pp. 32-35.*
He et al., Stem Cells 25: 69-77, 2007.*
Kirschstein, R. and Skirboll, LR, Stem Cells, NIH, Chapter 5, pp. 43-58, Jun. 2001.*
Bjornson et al., Science 283: 534-537, 1999.*
Stem cell Information. The National Inst of Health resource of stem cell research, (3 pages)-Appendix A.*
Kim et al. Regeneration and Transplantation, 13: 1185-1188, 2002.*
Blau et al. Cell, 105: 892-841, 2001.*
Seta and Kuwana, Keio J Med 56: 41-47, 2007.*
Fernandez Pujol, B. et al. "Endothelial-like cells derived from human CD14 positive monocytes," *Differentiation*, vol. 65: No. 5: 287-300, 2000.
Heinemann, D. E. H. et al. "Alkaline Phosphatase Expression during Monocyte Differentiation," *Immunobiology*, vol. 202: No. 1: 68-81, 2000.
Kuwana, M. et al. "Human circulating $CD14^+$ monocytes as a source of progenitors that exhibit mesenchymal cell differentiation," *Journal of Leukocyte Biology*, vol. 74: No. 5:833-845, Nov. 2003.
Schmeisser A., et al. "Monocytes coexpress endothelial and macrophagocytic lineage markers and form cord-like structures in Matrigel® under angiogenic conditions," *Cardiovascular Research*, vol. 49: No. 3: 671-680, 2001.
Zhao, Y. et al. "A human peripheral blood monocyte-derived subset acts as pluripotent stem cells," *Proc. Natl. Acad. Science*, vol. 100: No. 5: 2426-2431, Mar. 4, 2003.
Grounds et al., "The Role of Stem Cell in Skeletal and Cardiac Muscle Repair", *The Journal of Histochemistry & Cytochemistry*, vol. 50, No. 5, p. 589-610, 2002.
Zhao et al., "Human Bone Marrow Stem Cells Exhibit Neural Phenotypes and Ameliorate Neurological Deficits after Grafting into the Ischemic Brain of Rats", *Experimental Neurology*, vol. 174, p. 11-20, 2002.
Supplementary European Search Report—European application No. EP 04721666: Jul. 18, 2006 (date of completion of search.)

* cited by examiner

Primary Examiner—Jeffrey Stucker
Assistant Examiner—Aditi Dutt
(74) Attorney, Agent, or Firm—Locke Lord Bissell & Liddell LLP

(57) ABSTRACT

The present invention is to provide a multipotent cell wherein the sufficient amount necessary can be stably and conveniently supplied with a minimum invasion, that will not cause rejection at the time of cell transplantation, that has a potential to differentiate into various cells such as mesenchymal cells including bone, cartilage, skeletal muscle and fat, endothelial cells, myocardial cells, neurons, mesenchymal cells, myocardial cells, endothelial cells, neurons induced to differentiate from the multipotent cell, and a therapeutic agent/treating method comprising these as active ingredient. Peripheral blood mononuclear cells (PMBC) are cultured on fibronectin-coated plastic plates for 7 to 10 days. The generating cell population with a fibroblast-like morphology is derived from circulating $CD14^+$ monocyte, with a unique phenotype of $CD14^+CD45^+CD34^+$ type I collagen$^+$. These cells have a potential to differentiate into mesenchymal cells including bone, cartilage, skeletal muscle and fat, endothelial cells, myocardial cells, and neurons under particular culture conditions.

9 Claims, 10 Drawing Sheets

FIG. 3
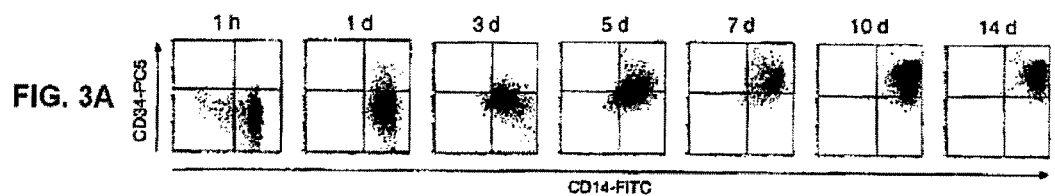
FIG. 3A
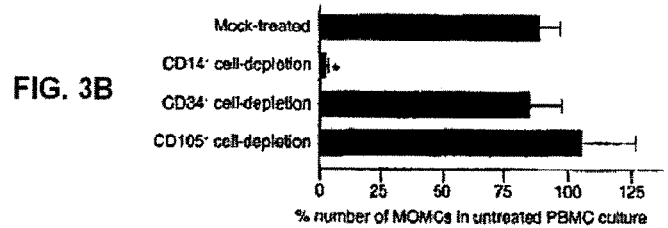
FIG. 3B
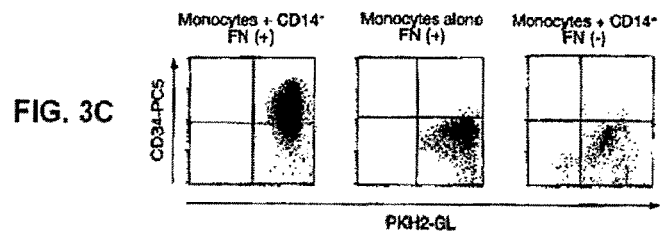
FIG. 3C
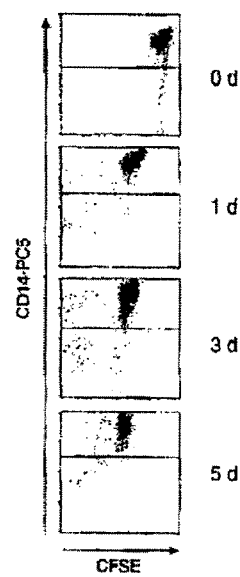
FIG. 3D FIG. 5
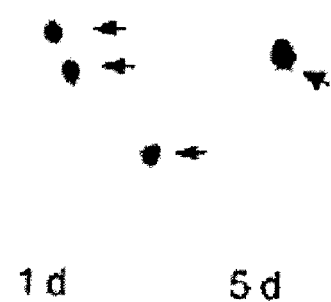
FIG. 5A
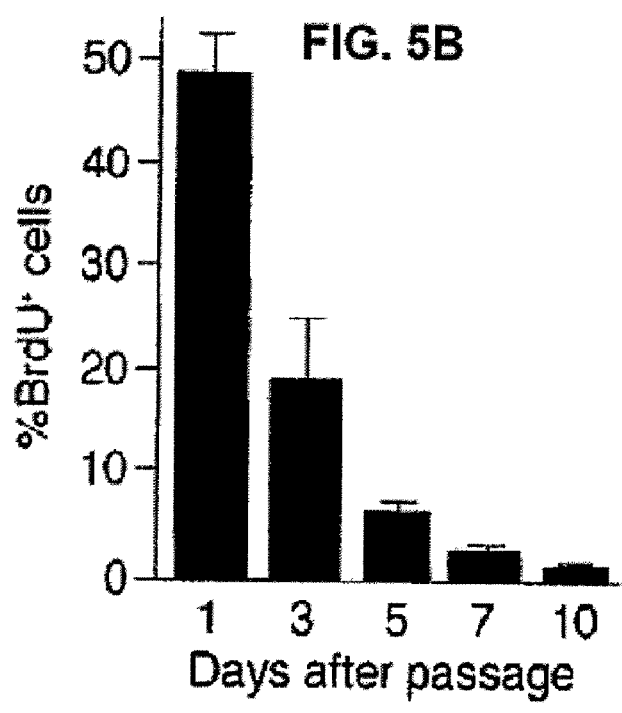
FIG. 5B
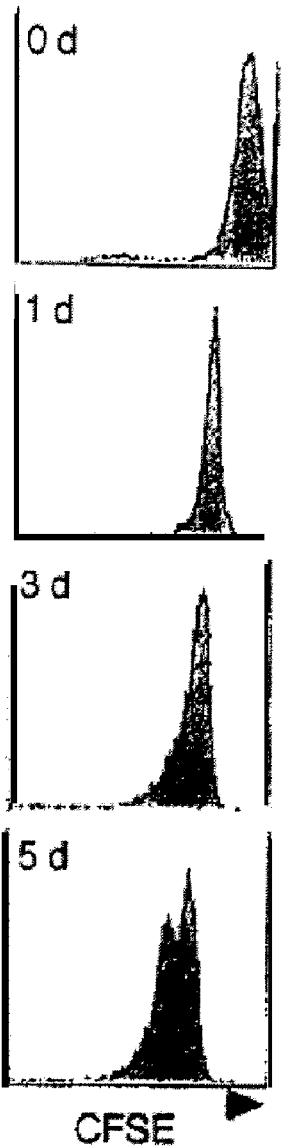
FIG. 5C

FIG. 8
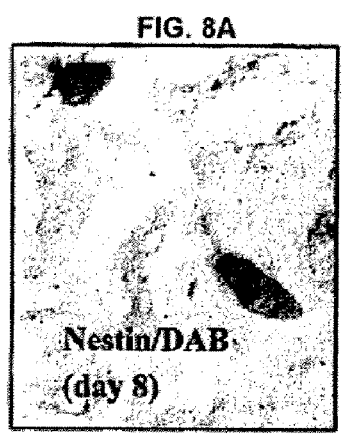
FIG. 8A
FIG. 8B
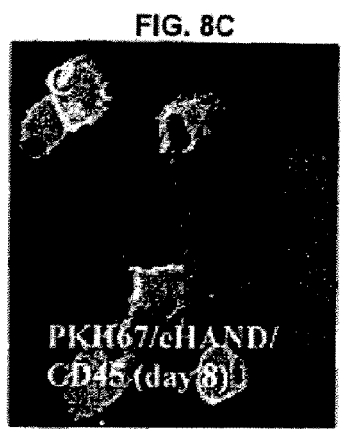
FIG. 8C
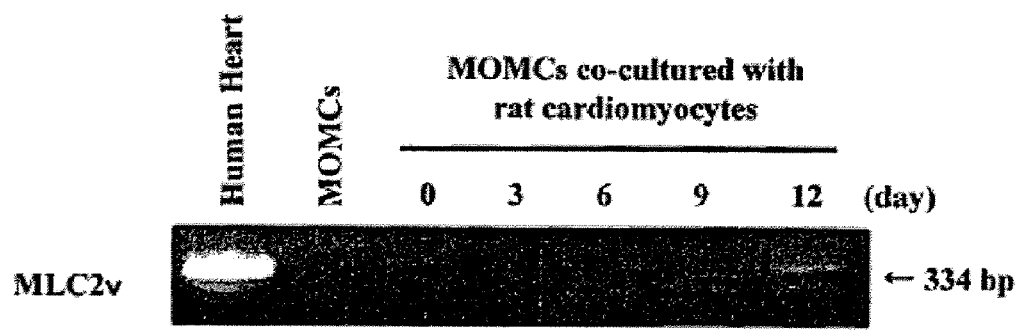
FIG. 8D FIG. 10
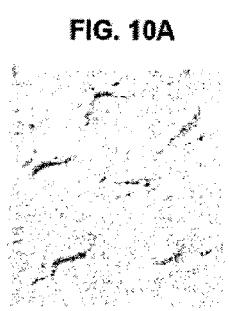
FIG. 10A
Phase contrast
(Day 7)
FIG. 10B
CD34    vWF
eNOS    VEGFR2/KDR
Immunohistochemistry
(Day 7)
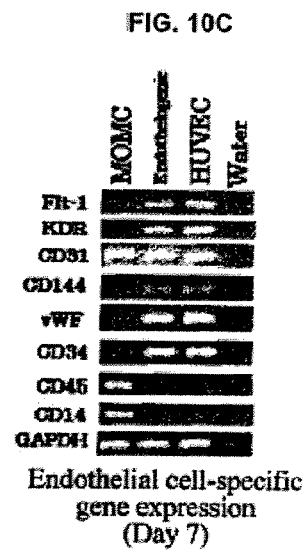
FIG. 10C
Endothelial cell-specific
gene expression
(Day 7)

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: MLC2v-sense primer

<400> SEQUENCE: 1
tgacaagaac gatctgagag                                              20

<210> SEQ ID NO 2
<211> LENGTH: 20
<212> TYPE: DNA
<213> ORGANISM: Artificial Sequence
<220> FEATURE:
<223> OTHER INFORMATION: MLC2v-antisense primer

<400> SEQUENCE: 2
caggttcttg tagtccaagt                                              20

<210> SEQ ID NO 3
<211> LENGTH: 21
<212> TYPE: DNA
<213> ORGANISM: Artificial Sequence
<220> FEATURE:
<223> OTHER INFORMATION: Osterix-sense primer

<400> SEQUENCE: 3
cttgtgcctg atacctgcac t                                            21

<210> SEQ ID NO 4
<211> LENGTH: 22
<212> TYPE: DNA
<213> ORGANISM: Artificial Sequence
<220> FEATURE:
<223> OTHER INFORMATION: Osterix-antisense primer

<400> SEQUENCE: 4
tcactctacc tgacccgtca tc                                           22

<210> SEQ ID NO 5
<211> LENGTH: 20
<212> TYPE: DNA
<213> ORGANISM: Artificial Sequence
<220> FEATURE:
<223> OTHER INFORMATION: Bone sialoprotein II-sense primer

<400> SEQUENCE: 5
aaacggcacc agtaccaaca                                              20

<210> SEQ ID NO 6
<211> LENGTH: 20
<212> TYPE: DNA
<213> ORGANISM: Artificial Sequence
<220> FEATURE:
<223> OTHER INFORMATION: Bone sialoprotein II-antisense primer

<400> SEQUENCE: 6
gccatcgtag ccttgtcctt                                              20

<210> SEQ ID NO 7
<211> LENGTH: 22
<212> TYPE: DNA
<213> ORGANISM: Artificial Sequence
<220> FEATURE:
<223> OTHER INFORMATION: Osteocalcin-sense primer

<400> SEQUENCE: 7
ggcagcgagg tagtgaagag ac                                           22

<210> SEQ ID NO 8
<211> LENGTH: 22
<212> TYPE: DNA

```
<213> ORGANISM: Artificial Sequence
<220> FEATURE:
<223> OTHER INFORMATION: Osteocalcin-antisense primer

<400> SEQUENCE: 8
ggcaagggga agaggaaaga ag                                              22

<210> SEQ ID NO 9
<211> LENGTH: 20
<212> TYPE: DNA
<213> ORGANISM: Artificial Sequence
<220> FEATURE:
<223> OTHER INFORMATION: SkM-MHC-sense primer

<400> SEQUENCE: 9
ataggaacac ccaagccatc                                                 20

<210> SEQ ID NO 10
<211> LENGTH: 20
<212> TYPE: DNA
<213> ORGANISM: Artificial Sequence
<220> FEATURE:
<223> OTHER INFORMATION: SkM-MHC-antisense primer

<400> SEQUENCE: 10
tttgcgtaga cccttgacag                                                 20

<210> SEQ ID NO 11
<211> LENGTH: 20
<212> TYPE: DNA
<213> ORGANISM: Artificial Sequence
<220> FEATURE:
<223> OTHER INFORMATION: Myogenin-sense primer

<400> SEQUENCE: 11
tggccttccc agatgaaacc                                                 20

<210> SEQ ID NO 12
<211> LENGTH: 20
<212> TYPE: DNA
<213> ORGANISM: Artificial Sequence
<220> FEATURE:
<223> OTHER INFORMATION: Myogenin-antisense primer

<400> SEQUENCE: 12
gcatcgggaa gagaccagaa                                                 20

<210> SEQ ID NO 13
<211> LENGTH: 22
<212> TYPE: DNA
<213> ORGANISM: Artificial Sequence
<220> FEATURE:
<223> OTHER INFORMATION: alpha1(II) collagen-sense primer

<400> SEQUENCE: 13
ttcagctatg gagatgacaa tc                                              22

<210> SEQ ID NO 14
<211> LENGTH: 20
<212> TYPE: DNA
<213> ORGANISM: Artificial Sequence
<220> FEATURE:
<223> OTHER INFORMATION: alpha1(II) collagen-antisense primer

<400> SEQUENCE: 14
agagtcctag agtgactgag                                                 20
```

<210> SEQ ID NO 15
<211> LENGTH: 23
<212> TYPE: DNA
<213> ORGANISM: Artificial Sequence
<220> FEATURE:
<223> OTHER INFORMATION: alpha1(X) collagen-sense primer

<400> SEQUENCE: 15
aatccctgga ccggctggaa ttc                                           23

<210> SEQ ID NO 16
<211> LENGTH: 23
<212> TYPE: DNA
<213> ORGANISM: Artificial Sequence
<220> FEATURE:
<223> OTHER INFORMATION: alpha1(X) collagen-antisense primer

<400> SEQUENCE: 16
ttgatgcctg gctgtcctgg acc                                           23

<210> SEQ ID NO 17
<211> LENGTH: 20
<212> TYPE: DNA
<213> ORGANISM: Artificial Sequence
<220> FEATURE:
<223> OTHER INFORMATION: PPARgamma-sense primer

<400> SEQUENCE: 17
aggagcagag caaagaggtg                                               20

<210> SEQ ID NO 18
<211> LENGTH: 20
<212> TYPE: DNA
<213> ORGANISM: Artificial Sequence
<220> FEATURE:
<223> OTHER INFORMATION: PPARgamma-antisense primer

<400> SEQUENCE: 18
aggactcagg gtggttcagc                                               20

<210> SEQ ID NO 19
<211> LENGTH: 22
<212> TYPE: DNA
<213> ORGANISM: Artificial Sequence
<220> FEATURE:
<223> OTHER INFORMATION: aP2-sense-primer

<400> SEQUENCE: 19
tatgaaagaa gtaggagtgg gc                                            22

<210> SEQ ID NO 20
<211> LENGTH: 22
<212> TYPE: DNA
<213> ORGANISM: Artificial Sequence
<220> FEATURE:
<223> OTHER INFORMATION: aP2-antisense-primer

<400> SEQUENCE: 20
ccaccaccag tttatcatcc tc                                            22

<210> SEQ ID NO 21
<211> LENGTH: 20
<212> TYPE: DNA
<213> ORGANISM: Artificial Sequence
<220> FEATURE:

<223> OTHER INFORMATION: CD34-sense primer

<400> SEQUENCE: 21
cctcccaagt tttaggacaa                                                   20

<210> SEQ ID NO 22
<211> LENGTH: 20
<212> TYPE: DNA
<213> ORGANISM: Artificial Sequence
<220> FEATURE:
<223> OTHER INFORMATION: CD34-antisense primer

<400> SEQUENCE: 22
cagctggtga taagggttag                                                   20

<210> SEQ ID NO 23
<211> LENGTH: 21
<212> TYPE: DNA
<213> ORGANISM: Artificial Sequence
<220> FEATURE:
<223> OTHER INFORMATION: CD45-sense primer

<400> SEQUENCE: 23
aacctgaagt gatgattgct g                                                 21

<210> SEQ ID NO 24
<211> LENGTH: 20
<212> TYPE: DNA
<213> ORGANISM: Artificial Sequence
<220> FEATURE:
<223> OTHER INFORMATION: CD45-antisense primer

<400> SEQUENCE: 24
tacctcttct gtttccgcac                                                   20

<210> SEQ ID NO 25
<211> LENGTH: 20
<212> TYPE: DNA
<213> ORGANISM: Artificial Sequence
<220> FEATURE:
<223> OTHER INFORMATION: CD14-sense primer

<400> SEQUENCE: 25
ctgcgtgtgc tagcgtactc                                                   20

<210> SEQ ID NO 26
<211> LENGTH: 20
<212> TYPE: DNA
<213> ORGANISM: Artificial Sequence
<220> FEATURE:
<223> OTHER INFORMATION: CD14-antisense primer

<400> SEQUENCE: 26
cgtccagtgt caggttatcc                                                   20

<210> SEQ ID NO 27
<211> LENGTH: 20
<212> TYPE: DNA
<213> ORGANISM: Artificial Sequence
<220> FEATURE:
<223> OTHER INFORMATION: Cbfa1/Runx2-sense primer

<400> SEQUENCE: 27
gtcttacccc tcctacctga                                                   20

<210> SEQ ID NO 28
<211> LENGTH: 20
<212> TYPE: DNA
<213> ORGANISM: Artificial Sequence
<220> FEATURE:
<223> OTHER INFORMATION: Cbfa1/Runx2-antisense primer

<400> SEQUENCE: 28
tgcctggctc ttcttactga                                      20

<210> SEQ ID NO 29
<211> LENGTH: 22
<212> TYPE: DNA
<213> ORGANISM: Artificial Sequence
<220> FEATURE:
<223> OTHER INFORMATION: MyoD-sense primer

<400> SEQUENCE: 29
cctagactac ctgtccagca tc                                   22

<210> SEQ ID NO 30
<211> LENGTH: 20
<212> TYPE: DNA
<213> ORGANISM: Artificial Sequence
<220> FEATURE:
<223> OTHER INFORMATION: MyoD-antisense primer

<400> SEQUENCE: 30
ggcggaaact tcagttctcc                                      20

<210> SEQ ID NO 31
<211> LENGTH: 21
<212> TYPE: DNA
<213> ORGANISM: Artificial Sequence
<220> FEATURE:
<223> OTHER INFORMATION: Sox-9-sense primer

<400> SEQUENCE: 31
cccgatctga agaaggagag c                                    21

<210> SEQ ID NO 32
<211> LENGTH: 21
<212> TYPE: DNA
<213> ORGANISM: Artificial Sequence
<220> FEATURE:
<223> OTHER INFORMATION: Sox-9-antisense primer

<400> SEQUENCE: 32
gttcttcacc gacttcctcc g                                    21

<210> SEQ ID NO 33
<211> LENGTH: 19
<212> TYPE: DNA
<213> ORGANISM: Artificial Sequence
<220> FEATURE:
<223> OTHER INFORMATION: GAPDH-sense primer

<400> SEQUENCE: 33
tgaacgggaa gctcactgg                                       19

<210> SEQ ID NO 34
<211> LENGTH: 20
<212> TYPE: DNA
<213> ORGANISM: Artificial Sequence
<220> FEATURE:
<223> OTHER INFORMATION: GAPDH-antisense primer

```
<400> SEQUENCE: 34
tccaccaccc tgttgctgta                                          20
```

MONOCYTE-ORIGIN MULTIPOTENT CELL MOMC

TECHNICAL FIELD

The present invention relates to a monocyte-derived multipotent cell of $CD14^+$ and $CD34^+$ that can differentiate into mesoderm cells such as mesenchymal cells, myocardial cells, and endothelial cells or into neurons; a mesodermal cell/tissue such as mesenchymal cell, myocardial cell and endothelial cell, and neuron/nerve tissue induced to differentiate from the monocyte-derived multipotent cell; a therapeutic agent comprising these as active ingredient; and to a treating method comprising administering these.

BACKGROUND ART

Peripheral blood monocytes are derived from bone marrow hematopoietic stem cells and are known to differentiate into several phagocytes, including macrophages, dendritic cells, osteoclasts, microglial cells of central nervous system, and liver Kupffer cells (Bioessays, 17, 977-986, 1995; Blood, 98, 2544-5254, 2001; BMC Immunol., 3, 15, 2002; Microsc Res Tech., 39, 350-364, 1997). The differentiation of the monocytes into various phagocytes is controlled by signaling of various growth factors. In other words, differentiation into macrophages, dendritic cells, osteoclasts are controlled by signaling of M-CSF, GM-CSF and IL-4, and receptor activating factors of NF ligand or M-CSF, respectively (see for example, Blood, 98, 2544-5254, 2001; BMC Immunol., 3, 15, 2002; J Exp Med., 190, 1741-1754, 1999). Until recently, it was believed that the differentiation potential of monocytes was restricted to phagocytes. However, recent studies have shown that human monocytes can differentiate into endothelial-like cells by culturing in vitro with a combination of angiogenic factors (see for example, Differentiation, 65, 287-300, 2000; Cardiovascular Res., 49, 671-680, 2001). In addition, the expression of bone-specific alkaline phosphatase was reported during the monocyte differentiation process in the in vitro granuloma model (see for example, Immunobiology, 202, 68-81, 2000). However, the differentiation potential is not completely clarified and it was not known whether monocytes had differentiation potential into cell types other than phagocytes.

On the other hand, it was revealed that many adult tissues contain populations of stem cells that can self-replicate and give rise to daughter cells that undergo an irreversible terminal differentiation (see for example, Science, 287, 1442-1446, 2000). The best-characterized are hematopoietic stem cells and their progeny, but stem cells are identified in most of the tissues, including mysenchymal, neuron, and hemotopoietic cells (see for example, Science, 284, 143-147, 1999; Science, 287, 1433-1438, 2000; J. Hepatol., 29, 676-682, 1998). Mesenchymal stem cells (MSCs) are identified as adherent fibroblast-like cells in the bone marrow with differentiation potential into mesenchymal tissues, including bone, cartilage, fat, muscle, and bone marrow stroma (see for example, Science, 284, 143-147, 1999). Recently, mesenchymal progenitors having morphologic and phenotypic features and differentiation potentials similar to MSCs have been reported at extremely low frequencies in umbilical cord blood (see for example, Br. J. Haematol., 109, 235-242, 2000), as well as in fetal (see for example, Blood, 98, 2396-2402, 2001) and adult peripheral blood (see for example, Arthritis Res., 2, 477-488, 2000). However, MSCs and circulating MSC-like cells do not express various hematopoietic markers or the stem cell/endothelial marker CD34 (see for example, Science, 284, 143-147, 1999; Br. J. Haematol., 109, 235-242, 2000; Blood, 98, 2396-2402, 2001).

As described above, various postnatal tissue-specific stem cells and embryonic stem (ES) cells are currently being analyzed as candidate sources for future therapeutic intervention for tissue regeneration (see for example, Science, 287, 1442-1446, 2000). It has been reported that bone marrow-derived MSCs engraft in many organs and differentiate along tissue-specific lineages upon its transplantation in animal models (see for example, Nat. Med., 6, 1282-1286, 2000; Science, 279, 1528-1530, 1998), as well as in human infant suffering osteogenesis imperfecta (see for example, Nat. Med., 5, 309-313, 1999). However, MSCs are rare in adult human bone marrow (0.01% to 0.001%), and expansion of MSCs to the number of cells required for regeneration therapy is technically difficult, expensive, and time-consuming (see for example, Stem Cells, 19, 180-192, 2001). ES cells are multipotent cells derived from germinal cells that can be propagated indefinitely in vitro being still undifferentiated and induced to differentiate to most cell types in vivo (see for example, Trends Biotechnol., 18, 53-57, 2000). Although ES cells have been isolated from human, their use in research as well as therapeutic is cumbered by ethical considerations (see for example, Science, 287, 1397, 2000).

Several different precursors that can differentiate into endothelial or mesenchymal cell types have been reported in human postnatal peripheral blood, including endothelial cells (see for example, Science, 275, 964-967, 1997), smooth muscle cells (see for example, Circulation, 106, 1199-1204, 2002), and mesenchymal cells (see for example, Arthritis Res., 2, 477-488, 2000). In vitro expansion of endothelial and smooth muscle progenitors requires a combination of several growth factors (see for example, Science, 275, 964-967, 1997; Circulation, 106, 1199-1204, 2002). Mesenchymal progenitors can be expanded in a medium supplemented with 20% fetal bovine serum (FBS) without any additional growth factors, but their development in PBMC cultures was reported to be unaffected by eliminating $CD14^+$ cells (see for example, Arthritis Res., 2, 477-488, 2000). However, these endothelial or mesenchymal cells do not have the phenotypic characteristics to be positive to CD 14, CD45, CD34 and type I collagen.

The big object remaining in modern medicine is said to overcome deficiency of organs due to disease or external injuries or functional impairment. The only method that can be practiced today for treating such condition is organ transplantation. However, there are still many difficulties for spreading as an actual treating method, due to problems such as brain-death diagnosis or supply from donors. On the other hand, regenerative medicine intending regeneration of organs draws attention with the recent development of stem cells and developmental biology, and is expected as the direction of the medicine to advance in the 21st century. In animal models, functional recoveries of organs by transplantation of ES cells have been reported, while the application in human is stuffed due to rejection or ethical problems of the use of ES cells. Further, as various adult tissues stem cells (mesenchymal, blood vessels, liver etc.) are extremely few in vivo, the isolation thereof is technically difficult, and it is hard at the present time to obtain sufficient amount of cells for transplantation. Therefore, there are many problems to be solved before the regenerative medicine using ES cells or tissue stem cells can be applied to the actual medicine. Particularly, it is essential to supply cells having differentiation potential in a stable manner so that regenerative medicine becomes a reality.

The object of the present invention is to provide a multipotent cell that can differentiate into various cells such as mesenchymal cells including bone, cartilage, skeletal muscle and fat, endothelial cells, myocardial cells and neurons wherein a sufficient amount can be supplied stably with minimum invasion, without problems such as securing donors and rejection in cell transplant, and with less ethical considerations; a mesodermal progenitor/mesodermal cell/mesodermal tissue and a neuron/nerve tissue, such as mesenchymal cells, myocardiac cells, endothelial cells, being induced to differentiate from the multipotential cell; a therapeutic agent comprising these as active ingredient; and a treating method administering the same.

The present inventors confirmed the expression of fibroblast-like cells when peripheral blood mononuclear cells (PBMCs) are cultured on fibronectin-coated plastic plates for 7 to 10 days. Being interested by the origin and physiological function of this human cell population exhibiting a fibroblast-like morphology, the present inventors found that these cells are derived from circulating $CD14^+$ monocytes, with a unique phenotype of $CD14^+CD45^+CD34^+$ type I collagen$^+$, and having a potential to differentiate into mesenchymal cells including bone, cartilage, smooth muscle and fat, endothelial cells, myocardial cells, neurons, under a particular culture condition. They named this cell the monocyte-derived multipotent cell (MOMC). With the knowledge having revealed for the first time that circulating monocytes are multipotent progenitors having a differentiation potential not only into phagocytes but also into various mesenchymal cells, the present inventors have thus completed the invention.

DISCLOSURE OF THE INVENTION

In other words, the present relation relates to: a monocyte-derived multipotent cell, derived from a monocyte, which expresses CD14 and CD 34 ("1"); a monocyte-derived multipotent cell, derived from a monocyte, which expresses CD14, CD34, CD45 and type I collagen ("2"); the monocyte-derived multipotent cell according to "1" or "2", that can differentiate into mesenchymal cells by a culture under a condition inducing differentiation into mesenchymal tissues ("3"); the monocyte-derived multipotent cell according to "3", wherein the mesenchymal cells are osteoblasts, skeletal myoblasts, chondrocytes or adipocytes ("4"); the monocyte-derived multipotent cell according to "1" or "2", that can differentiate into myocardial cells by a culture under a condition inducing differentiation into cardiac muscle such as a coculture with cultured myocardial cells ("5"); the monocyte-derived multipotent cell according to "1" or "2", that can differentiate into neuron by a culture under a condition inducing differentiation into nerve, such as a coculture with cultured neuron ("6"); the monocyte-derived multipotent cell according to "1" or "2", that can differentiate into endothelial cells, by a culture under a condition inducing differentiation into endothelium such as a culture under a condition maintaining endothelial cells ("7"); and the monocyte-derived multipotent cell according to "1" or "2", that can differentiate into mesodermal cells ("8").

Furthermore, the present invention relates to a method for preparing a monocyte-derived multipotent cell, comprising culturing peripheral blood mononuclear cells (PBMCs) in vitro on fibronectin, and collecting fibroblast-like cells expressing CD14 and CD34 ("9"); the method for preparing a monocyte-derived multipotent cell according to "9", comprising culturing in vitro on fibronectin for 5 to 14 days ("10"); a mesenchymal progenitor, a mesenchymal cell or a mesenchymal tissue induced by culturing the monocyte-derived multipotent cell according to any one of "1" to "8", under a condition inducing differentiation into mesenchymal tissues ("11"); the mesenchymal progenitor, the mesenchymal cell or the mesenchymal tissue according to "11", wherein the mesenchymal cells are osteoblasts, skeletal myoblasts, chondrocytes or adipocytes ("12"); a myocardial progenitor, a myocardial cell or a myocardial tissue induced by culturing the monocyte-derived multipotent cell according to any one of "1" to "8", under a condition inducing differentiation into cardiac muscle such as a coculture with cultured myocardial cells ("13"); a neural progenitor, a neuron or a nerve tissue induced by culturing the monocyte-derived multipotent cell according to any one of "1" to "8", under a condition to inducing differentiation into nerve, such as a coculture with cultured neuron ("14"); an endothelial progenitor, an endothelial cell or an endothelial tissue induced by culturing the monocyte-derived multipotent cell according to any one of "1" to "8", under a condition inducing differentiation into endothelium, such as a culture under a condition maintaining endothelial cells ("15"); a mesodermal progenitor, a mesodermal cell or a mesodermal tissue induced to differentiate from the monocyte-derived multipotent cell according to any one of "1" to "8" ("16").

Moreover, the present invention relates to a therapeutic agent comprising as active ingredient the monocyte-derived multipotent cell according to any one of "1" to "8" and/or mesodermal progenitors, mesodermal cells and/or mesodermal tissues induced to differentiate from the monocyte-derived multipotent cell ("17"); or a therapeutic agent comprising as active ingredient the monocyte-derived multipotent cell according to any one of "1" to "8" and/or neural progenitors, neurons and/or nerve tissues induced to differentiate from the monocyte-derived multipotent cell ("18"); a treating method comprising administering the monocyte-derived multipotent cell according to any one of "1" to "8" and/or mesodermal progenitors, mesodermal cells and/or mesodermal tissues induced to differentiate from the monocyte-derived multipotent cell ("19"); or a treating method comprising administering the monocyte-derived multipotent cell according to any one of "1" to "8" and/or neural progenitors, neurons and/or nerve tissues induced to differentiate from the monocyte-derived multipotent cell ("20").

BRIEF DESCRIPTION OF THE DRAWINGS

(FIG. 1A, FIG. 1B) PBMCs were cultured on fibronectin in low-glucose DMEM supplemented with 10% FBS for 7 days, and observed with a phase contrast microscope. The original magnifications are ×80 for FIG. 1A, and ×40 for FIG. 1B. MOMCs were moved on a new fibronectin-coated plate and cultured for 24 hours. FIG. 1C shows the observation results with a phase contrast microscope (×40). FIGS. 1D-E show observation results with an electron microscope (FIG. 1D and FIG. 1E, ×5000; FIG. 1F and FIG. 1G, ×30000). A bundle of intermediate filaments is shown by an arrow, and a structure similar to a rod-shaped microtubulated body is shown by an arrowhead. L is for labyrinth-like endocytic vesicle; LD is for lipid droplet; N is for nucleus, and PS is for pseudopodia.

FIGS. 3A-D demonstrate that MOMCs of the present invention originate from circulating CD14+ monocytes. (FIG. 3A) PBMCs were cultured on fibronectin for 1 hour, and 1, 3, 5, 7, 10, and 14 days. The adherent cells were harvested and stained with FITC-conjugated anti-CD14 and PC5-conjugated anti-CD34 mAbs and analyzed by flow cytometry. The results shown are representative of three independent experiments. (FIG. 3B) PBMCs depleted of CD14+ cells, CD34+ cells or CD 105+ cells, and mock-treated PMBCs were cultured on fibronectin for 7 days. The number of attaching cells per cm3 was counted, and the results are expressed as the ratio to the number of attached cells in the untreated PBMC culture. The results shown are the mean and SD from three donors. The asterisk in the figure indicates a significant difference compared with mock-treated PBMC cultures. (FIG. 3C) MACS (Magnetic Cell Sorting)-sorted CD14+ monocytes were stained with PKH67 and cultured with or without unlabeled CD14− cells (ratio 1:4) on fibronectin-coated or uncoated plastic plates for 7 days. The adherent cells were harvested, stained with PC5-conjugated anti-CD34 mAb, and analyzed by flow cytometry. The results shown are representative of three experiments. (FIG. 3D) MACS-sorted CD14+ monocytes were stained with CFSE and cultured on fibronectin for 0, 1, 3, and 5 days. The adherent cells were harvested and stained with PC5-conjucated anti-CD14 mAb. The cells were analyzed by flow cytometry. The results shown are representative of three experiments.

FIGS. 5A-C show how the MOMCs of the present invention proliferate. MOMCs generated by culturing PBMCs on fibronectin-coated plates for 7 days were moved on fibronectin-coated chamber slides. MOMCs were further cultured for 1, 3, 5, 7, and 10 days, and stained with BrdU. The nuclei were counterstained with hematoxylin. (FIG. 5A) A representative figure at Day 1 and Day 5. The arrow indicates nuclei positive for BrdU staining. (FIG. 5B) At least 200 cells were counted to see the BrdU staining experiment result and the number of BrdU+ cells was calculated for individual slides cultured for 1, 3, 5, 7, and 10 days. The results shown are the mean and SD of five independent experiments. (FIG. 5C) MOMCs were labeled with CFSE and were cultured on new fibronectin-coated plates for 0, 1, 3, 5 days. The adherent cells were collected and analyzed by flow cytometry. The results shown are representative of three independent experiments.

FIGS. 8A-D show how MOMCs of the present invention differentiate into myocardium. Nestins (brown) expressed in MOMCs cocultured with Wistar rat-cultured myocardial cells for 8 days were immunostained (FIG. 8A ×200). After labeling cell membrane with fluorescent PKH67 (green), MOMCs were cocultured with Wistar rat-cultured myocardial cells for 7 days, and were double fluorescently immunostained with Nkx 2.5 (red), a myocardial cell-specific transcription factor, and CD45 (blue), a hematopoietic marker (FIG. 8B ×200). After labeling cell membrane with fluorescent PKH67 (green), MOMCs were cocultured with Wistar rat-cultured myocardial cells for 8 days, and were double fluorescently immunostained with eHAND (red), a myocardial cell-specific transcription factor, and CD45 (blue), a hematopoietic marker (FIG. 8C ×200). MOMCs were cocultured with Wistar rat-cultured myocardial cells for 3, 6, 9, 12 days and expression of the mRNAs for myosin light chain (MLC2v), a myocardial cell-structural protein (FIG. 8D). The results shown are representative of three experiments.

FIGS. 10A-C show how MOMCs of the present invention differentiate into endothelial cells. MOMCs induced to differentiate in a EBM-2 medium, a maintenance medium of endothelia cells, for 7 days, changed to a morphology having multiple projections from a spindle shape (FIG. 10A ×200). CD34 and endothelial cell-specific vWF, eNOS, VEGFR2/KDR/Flk-1, expressed in MOMCs induced to differentiate in an EBM-2 medium for 7 days, were immunostained (brown) (FIG. 10B ×200). Expression of the mRNAs for Flt-1, VEGFR2/KDR/Flk-1, CD31, CD144, vWF, CD34, CD45, CD14, and GAPDH, expressed in endothelial cells after 7-day culture of MOMCs in an EBM-2 medium, was examined (FIG. 10C). The results shown are representative of three experiments.

BEST MODE OF CARRYING OUT THE INVENTION

Figure 1:
FIGS. 1A-G show the morphology of MOMCs of the present invention.
Figure 1:
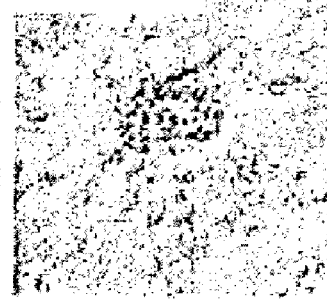
Figure 1:
Figure 1:
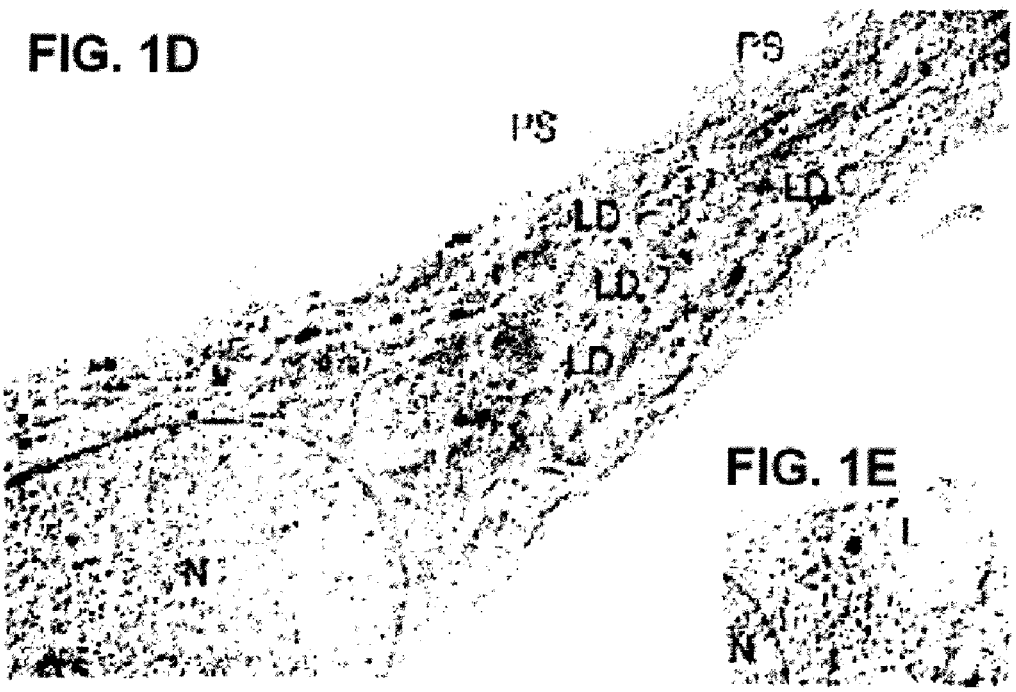
Figure 1:
Figure 1:
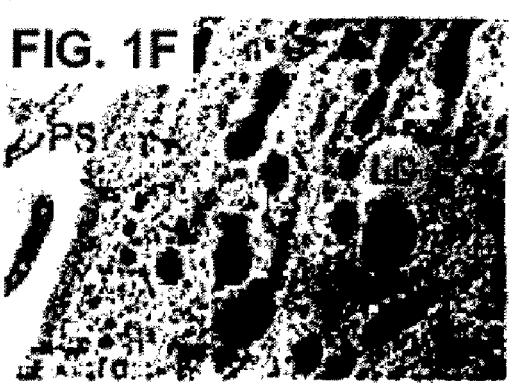
Figure 1:

As for the monocyte-derived multipotent cell (MOMC) of the present invention, there is no specific limitation as long as it is derived from a monocyte, and it is a cell or a cell population expressing CD14, CD34, CD45 and type I collagen, derived from a cell, a cell population or a monocyte expressing CD14 and CD34. The origin of the above monocytes is not particularly limited including mice, rats, dogs, pigs, monkey and human, and human being preferable. As for human monocyte, it can be a monocyte from a donor, while an autologous one is preferable. As for the source of monocytes, monocytes derived from peripheral blood or bone marrow, or monocytes differentiated from hematopoietic stem cells ex vivo can be exemplified. The monocytes herein mentioned are defined to be positive to CD14 or CD11b.

The above-mentioned CD14 and CD45 are known to be a marker of monocyte and cell derived from monocyte, CD34 a marker of endothelial and stem cells, and type I collagen a marker of mesenchymal cells. As for the monocyte-derived multipotent cell of the present invention, those expressing CD105 and Sca-1 as stem cell markers, type III collagen and fibronectin as mesenchymal cell markers, and VE cadherin and Flt-1 as endothelial markers are preferable. The MOMCs are cells distinct from monocytes, macrophages or dendritic cells from their protein expressing pattern mentioned above, and it can be said that MOMCs are a new cell population having combined the characteristics of mesenchymal cells, endothelial cells and stem cells.

The MOMCs of the present invention are derived from circulating CD14$^+$ monocytes, as cited in the following. First, MOMCs are positive for the monocyte lineage markers CD14, CD13, CD11b, CD11c and CD64. Second, serial phenotypic analyses of adherent peripheral blood cells cultured on fibronectin showed increased expression of CD34 on the adherent CD14$^+$ cells. Third, the development of MOMCs was almost completely inhibited by depleting the PBMCs of CD14$^+$ cells, but not by depleting the PBMCs of cells positive for CD34 or CD105. Finally, studies using labeled-CD14$^+$ cells revealed up-regulated expression of CD34 on CD14$^+$ monocytes, and that there was no cell proliferating rapidly in PBMC cultures among the CD14$^-$ cell population.

As for the MOMCs of the present invention, a cell with multipotency that can differentiate into mesodermal cells under induction condition known to differentiate MSC into mesodermal cells is preferable, particularly a cell with multipotency that can differentiate into mesenchymal cells such as osteoblasts, skeletal myoblasts, chondrocytes, adipocytes, bone marrow stromal cells and smooth muscle cells, by a culture under a condition inducing differentiation into mysenchymal tissues; multipotency that can differentiate into myocardial cells by a culture under a condition inducing differentiation into cardiac muscle such as a coculture with cultured myocardial cells; multipotency that can differentiate into endothelial cells, by a culture under a condition inducing differentiation into endothelium, such as a culture under a condition maintaining endothelial cells; as well as multipotency that can differentiate into neurons that are ectodermal cells, by a culture under a condition inducing differentiation into nerve, such as a coculture with cultured neuron.

Furthermore, the present invention relates to a mesodermal progenitor, a mesodermal cell or a mesodermal tissue induced to differentiate from the MOMCs of the present invention under induction condition known to differentiate MSC to mesodermal cells; for instance a mesenchymal progenitor, a mesenchymal cell or a mesenchymal tissue such as osteoblasts, skeletal myoblasts, chondrocytes and adipocytes, induced by a culture under a condition inducing differentiation of MOMCs into mesenchymal tissues; a myocardial progenitor, a myocardial cell, or a myocardial tissue induced by a culture under a condition inducing differentiation of MOMCs into cardiac muscle such as a coculture with cultured myocardial cells; an endothelial progenitor, an endothelial cell or an endothelial tissue induced by a culture under a condition inducing differentiation of MOMCs into endothelium, such as a culture under a condition maintaining endothelial cells; as well as an ectodermal neural progenitor, a neuron or a nerve tissue induced by a culture under a condition inducing differentiation of MOMCs into nerve, such as a coculture with cultured neuron.

The osteoblasts induced by culturing under a condition inducing differentiation into osteoblasts, are preferably cells with a cylinder-like form, being Alizarin red positive for calcium deposition, alkaline phosphatase staining positive, showing increase of intracellular Ca concentration, and expressing bone sialoprotein II, osteocalcin gene specific to osteoblasts. The chondrocytes induced by a culture under a condition inducing differentiation into chondrocytes are preferably cells slightly large with a cylinder shape, rich of cytoplasm, and expressing type II and X collagens, which are specific to chondrocytes. The skeletal muscle cells induced by culturing under a condition inducing differentiation into skeletal muscle cells, are preferably cells with a long spindle shape, expressing skeletal muscle-specific actin and myocin. The adipocytes induced by a culture under a condition inducing differentiation into adipocytes are preferably cells with lipid droplets for Oil-red staining, wherein PPARγ and aP2 genes expression is enhanced.

As for the myocardial progenitors or myocardial cells induced by a culture under a condition inducing differentiation into myocardial, cells expressing Nestin, myocardial-specific transcription factors Nkx2.5 and eHAND, and myosin light chain gene, a myocardial cell-structural protein, can be preferably exemplified. As for the neural progenitors or neurons induced by a culture under a condition inducing differentiation into nerve, cells expressing Nestin, and neuron-specific transcription factors NeuroD, Neurogenin 2, and then expressing Hu, and NeuN being nerve markers can be preferably exemplified. As for the endothelial progenitors or endothelial cells induced by a culture under a condition inducing differentiation into endothelium, cells with a polymorphic form with small projections, expressing endothelial-specific marker protein, KDR, vWF and eNOS can be preferably exemplified.

As described in the above, MOMCs have a differentiation potential into mesodermal cells such as mesenchymal cells under induction condition known to mainly differentiate MSC into mesodermal cells, as well as a differentiation potential into neurons of ectodermal system induced by a culture under a condition inducing differentiation of MOMCs into nerve. Moreover, the differentiation of MOMCs into mesodermal cells such as individual mesenchymal cells follows the steps observed in MSC differentiation, in terms of the timing of lineage-specific transcription factor expression. For example, the expression of Cialoprotein II and osteocalcin follows the expression of Cbfa1/Runx2 (Cell, 108, 17-29, 2002), and further, the expression of MyoD precedes the expression of SkM-actin and myosin (Front Biosci., 5, D750-767, 2000). These findings suggest that differentiation processes into individual mesenchymal lineages are shared by MOMCs and MSCs.

As for the preparation method of MOMCs of the present invention, there is no specific limitation as long as it is a method comprising culturing peripheral blood mononuclear cells (PBMCs) in vitro on fibronectin, for example on plastic plates coated with fibronectin preferably for 5 to 14 days, more preferably for 7 to 10 days, and collecting fibroblast-like cells expressing CD14 and CD34, but it is preferable to culture PBMCs without any additional growth factors. Collagen or laminin can be used instead of the above-mentioned fibronectin, but the differentiation of monocytes into MOMCs requires soluble factors derived from $CD14^-$ cells beside fibronectin. The origin of the above PBMCs is not particularly limited including experimental animals such as mice, rats, dos, pigs and monkeys or human, while human PBMCs can be preferably exemplified. Moreover, human PBMCs can be isolated from human venous blood by common methods. The above-mentioned culturing method is not limited, and a culturing method comprising culturing at 37° C., with 5% $CO_2$ in a humidified atmosphere, at a density of $10^4$ to $10^7$/ml, for example at $2 \times 10^6$/ml, and depleting non-adherent cells and supplementing a fresh medium every 2 to 4 days, more preferably every 3 days. Thus obtained MOMCs of the present invention can be expanded in culture without loosing their original phenotype for up to 5 passages.

The present invention relates to a therapeutic agent comprising as active ingredient the MOMCs of the present invention and/or mesodermal progenitors, mesodermal cells and/or mesodermal tissues induced to differentiate from the MOMCs, for instance, mesenchymal progenitors such as osteoprogenitors, skeletal muscle progenitors, chondroprogenitors, adipoprogenitors, mesenchymal cells such as osteoblasts, skeletal myoblasts, chondrocytes and adipocytes, mesenchymal tissue such as bone, cartilage, muscle and fat, induced by culturing MOMCs under a condition inducing differentiation into mesenchymal tissues; myocardial progenitors, myocardial cells or myocardial tissues induced by culturing MOMCs under a condition inducing differentiation into cardiac muscle, such as a coculture with cultured myocardial cells; endothelial progenitors, endothelial cells, endothelial tissues induced by culturing MOMCs under a condition inducing differentiation into endothelium such as a culture under a condition maintaining endothelial cells. The present invention also relates to a therapeutic agent comprising as active ingredient the MOMCs of the present invention and/or neural progenitors, neurons and/or nerve tissues induced to differentiate from the MOMCs. Further, it relates to a treating method comprising administering the MOMCs of the present invention and/or the mesodermal progenitors, mesodermal cells and/or mesodermal tissues, the neural progenitors, neurons and/or nerve tissues induced to differentiate from the MOMCs, for example administering directly to an impaired or deleted site or to its proximity or to the peripheral blood. It is preferable to determine appropriately either of MOMCs or MOMCs treated by inducing differentiation are suitable for the therapeutic agent, according to the type of cells or diseases, or administering method. Further, as MOMCs are cells relatively easy to transfer genes, it can be used for tissue reconstitution therapy after introducing a particular gene before cell transplantation to human. For example, when there is some osteogenic impairment in a certain congenital disease, it is possible to transplant after modifying the gene or to prepare it to generate a particular protein (cytokine, growth factor, hormone, etc.).

As described above, as MOMCs have a potential to differentiate into mesodermal tissue such as various mesenchymal tissues or nerve tissues, they are useful as a source of cells for tissue regenerating therapy to congenital diseases, degenerative diseases, and injuries. For instance, as for disease or pathology to be the object of the therapeutic agent or treating method of the present invention, bone destruction due to degenerative disease such as dysostosis, fracture, rheumatoid arthritis; cartilage destruction due to rheumatoid arthritis or osteoarthritis, or muscular disease due to congenital disease such as dystrophy or acquired disease such as myositis; myocardial disease due to myocardial infarction or cardiomyopathy, brain disorder such as brain infarction or Parkinson disease; injury such as spinal cord damage, or vascular disease due to arteriosclerosis or connective tissue disease. Moreover, plastic surgery such as breast augmentation and the like is encompassed in the therapeutic agent or treating method of the present invention for convenience. In cell therapy using MOMCs or MOMCs treated by inducing differentiation, there are considerable advantages over currently proposed regenerative treatment using tissue-specific stem cells and ES cells. In other words, as a large number of monocytes can be obtained from patients by collecting their blood, a minimally invasive procedure, circulating monocytes could be a relatively easy source of autologous cells. Furthermore, the generation of MOMCs from monocytes is technically easy and quick, and the ethical dilemma of using ES cells can be bypassed.

The present invention will be explained in detail in the following, but the technical scope of the present invention will not be limited to these examples.

METHODS AND MATERIALS

Example 1

MOMC Cultures

PMBCs were isolated from heparinized venous blood obtained from healthy adult by Lymphoprep (Nycomed Pharma AS) density gradient centrifugation. All blood samples were obtained after the subjects gave their written informed consent, approved by the Institutional Review Boards. Isolated cells were washed twice with phosphate-buffered saline (PBS) and suspended in low-glucose DMEM supplemented with 10% heat-inactivated FBS (JRH Biosciences). PMBCs were cultured at a density of $2 \times 10^6$/ml on plastic plates coated with fibronectin without any additional growth factors at 37° C. with 5% $CO_2$, in a humidified atmosphere. Three days after the culture, non-adherent cells were removed. The medium was changed to a fresh one every three days and the cells were cultured for up to 4 weeks. After 7-10 days of culture, the adherent cells were collected as MOMCs and used in the following assays or were moved on new fibronectin-coated plates and maintained in the same culture condition for up to 10 passages.

To examine the origin of MOMCs, PBMCs depleted of $CD14^+$, $CD34^+$ or $CD105/endoglin/SH2^+$ cells were cultured on fibronectin-coated plates for 7 days. The depletion of $CD14^+$ or $CD34^+$ cells was performed by using an anti-CD14 or anti-CD34 monoclonal antibody coupled to magnetic beads (DynaBeads) followed by magnetic separation according to the manufacturer's protocol. $CD105^+$ cell-depleted PBMCs were prepared by incubating PBMCs with anti-CD105 mAb (Immunotech) and subsequently with goat anti-mouse IgG antibody coupled to magnetic beads (Dynal). Mock-treated PBMCs incubated with isotype-matched mouse mAb and bead-conjugated anti-mouse IgG antibody were also prepared as a control. The proportion of $CD14^+$ cells in the $CD14^+$ cell-depleted PBMC fraction was consistently <0.5%, and the proportions of $CD34^+$ cells in the $CD34^+$ cell-depleted fraction and of $CD105^+$ cells in the $CD105^+$ cell-depleted fraction were <0.01% by flow cytometry. The number of attaching cells per $cm^3$ was counted and the results were expressed as the ratio to the untreated PBMC culture.

Some experiments were performed to separate circulating $CD14^+$ monocytes and $CD14^-$ cells from PBMCs by using anti-CD14 mAb-coupled magnetic beads (CD14 MicroBeads; Miltenyi Biotech) followed by MACS column separation according to the manufacturer's protocol. Flow cytometric analysis revealed that monocyte and $CD14^-$ cell fractions contained >98% and <0.5% $CD14^+$, respectively. Monocytes were labeled with PKH67 green (Sigma) and cocultured with unlabeled $CD14^-$ cells (ratio of 1:4) on fibronectin-coated plastic plates for 7 days. PKH67-labeled monocytes were also cultured alone on fibronectin-coated or uncoated plastic plates for 7 days.

Example 2

Preparation of Macrophages and Dendritic Cells

Macrophages were prepared by culturing adherent PMBCs on plastic plates in M199 medium supplemented with 20% FBS and 4 ng/ml M-CSF (R&D Systems) for 7 days (Differentiation, 65, 287-300, 2000). Mature monocyte-derived dendritic cells were obtained from plastic adherent PBMCs by maturation using a series of culture conditions (J Immunol Methods, 196, 121-135, 1996). Briefly, adherent cells were cultured in RPMI1640 supplemented with 10% FBS containing 50 ng/ml GM-CSF and 50 ng/ml IL-4 (all from PeproTech) for 7 days. Next, the immature dendritic cells were incubated with 50 ng/ml TNF-α (PeproTech) for 3 days. Flow cytometric analysis revealed that the macrophage fraction contained 98% or more of $CD14^+CD80^+$ cells and the dendritic cell fraction contained 95% or more of $CD83^+HLA$-$DR^+$ cells and less than 1% of $CD14^+$ cells.

Example 3

Cell Lines

Primary cultures of human dermal fibroblasts were established from dermal biopsies of healthy donors and maintained in low-glucose DMEM supplemented with 10% FBS. Primary human myoblasts were prepared by culturing muscle biopsies from patients that are histologically normal even being clinically suspected as myositis (J Cell Biol., 144, 631-643, 1999). The human osteosarcoma cell line MG-63, the rhabdomyosarcoma cell line RD, and the chondrosarcoma cell line OUMS-27 were obtained from Health Science Research Resources Bank of Japan (Osaka, Japan) and maintained in low-glucose DMEM supplemented with 10% FBS.

Example 4

In Vitro Differentiation of MOMCs into Mesenchymal Cells

MOMCs which were either freshly generated from PBMCs, cultured for several passages or cryo-preserved, were moved on new fibronectin-coated plastic plates or chamber slides and grown to semi-confluence in high-glucose DMEM supplemented with 10% FBS (Hyclone Laboratories). Next, the cells were then cultured under conditions known to induce MSCs to differentiate into various mesenchymal cell types cited in the following (Science, 284, 143-147, 1999; J Cell Biol., 144, 631-643, 1999; J Cell Biochem., 64, 295-312, 1997; Muscle Nerve, 18, 1417-1426, 1995; Tissue Eng., 4, 415-428, 1998; Arthritis Rheum., 44, 85-95, 2001; J Biol Chem., 275, 9645-9652, 2000). Monocytes, macrophages, and dermal fibroblasts newly isolated from PBMCs were treated under identical conditions as controls.

As for osteogenesis, the adherent cells were cultured in Osteogenesis induction medium (Clonetics) containing 100 nM dexamethasone, 10 mM β-glycerophosphate, and 50 μM ascorbic acid. The medium was changed twice a week for 3 weeks.

As for myogenesis, the adherent cells were treated with 10 μM 5-azacytidine (Sigma) for 24 hours. The cells were washed with PBS and cultured in a medium containing 5% horse serum (Life Technologies), 50 mM hydrocortisone (Sigma) and 4 ng/ml basic fibroblast growth factor (Sigma). The medium was changed twice a week for 3 weeks.

As for chondrogenesis, the adherent monolayer cells were cultured for 3 weeks in serum-free medium in the presence of TGF-β (R & D systems), which was added to the culture medium every other day so that the final concentration become 10 ng/ml.

As for adipogenesis, the cells were incubated with adipogenic induction medium supplemented with 1 μM dexamethasone, 0.5 mM methyl-isobutylxanthine, 10 μg/ml insulin, and 100 mM indomethacin (all from Sigma). After 72 h, the medium was changed to maintenance medium supplemented with only 10 μg/ml insulin and rested for 24 hours. The cells were treated three times with adipogenic induction medium and maintained in the maintenance medium for an additional week.

Example 5

In Vitro Differentiation of MOMCs into Myocardial Cells

MOMCs were cocultured with cultured myocardial cells derived from Wistar rat fetus for 8 days. The cultured cells were fixed with 4% paraformaldehyde, and then immunostained (DAB staining) with human-specific anti-nestin antibody (Chemicon).

After labeling cell membrane with fluorescent PKH67 (Sigma), MOMCs were cocultured with Wistar rat cultured myocardial cells for 7 to 10 days. The cultured cells were fixed with 4% paraformaldehyde, and double fluorescently immunostained with anti-Nkx2.5 antibody, anti-eHAND antibody (Santa Cruz), and anti-CD45 antibody (DAKO).

MOMCs were cocultured with Wistar rat cultured myocardial cells for 3, 6, 9, and 12 days, and mRNA was extracted. Human specific PCR primers (TGACAAGAACGATCT-GAGAG (SEQ ID NO: 1), CAGGTTCTTGTAGTCCAAGT (SEQ ID NO: 2)) to myocin light chain (MLC2v) being a myocardial cell structural protein were constructed and RT-PCR was performed.

Example 6

In Vitro Differentiation of MOMCs into Neurons

MOMCs were cocultured with Wistar rat cultured neurons for 8 days. The cultured cells were fixed with 4% paraformaldehyde, and then immunostained with human-specific anti-nestin antibody (DAB staining).

After labeling cell membrane with fluoroscent PKH67, MOMCs were cocultured with Wistar rat cultured neurons for 4 days. The cultured cells were fixed with 4% paraformaldehyde, and double fluorescently immunostained with anti-NeuroD antibody (Santa Cruz) and anti-CD45 antibody (DAKO).

MOMCs were cocultured with Wistar rat cultured neurons for 3 days. The cultured cells were fixed with 4% paraformaldehyde, and double fluorescently immunostained with human-specific anti-nestin antibody and anti-Neurogenin 2 antibody (Chemicon).

After labeling cell membrane with fluoroscent PKH67, MOMCs were cocultured with Wistar rat cultured neurons for 9 to 10 days. The cultured cells were fixed with 4% paraformaldehyde, and double fluorescently immunostained with anti-Hu antibody and anti-NeuN antibody (Chemicon).

Example 7

In Vitro Differentiation of MOMCs into Endothelial Cells

MOMCs were cultured in endothelial cell maintenance medium EBM-2 (Clonetics) for 7 to 10 days as adherent cells. The cultured cells were fixed with 10% neutral buffered formalin, and immunostained (DAB staining) with anti-CD34 antibody (Calbiochem-Novabiochem), anti-vWF antibody (Dako), anti-eNOS antibody (Becton-Dickinson) and anti-VEGFR2/KDR/Flk-1 antibody (Sigma).

RNA was extracted from MOMCs cultured in EBM-2 medium for 7 days, and reverse-transcribed to cDNA. PCR was performed by using specific primers to Flt-1, VEGFR/2/KDR/Flk-1, CD31, CD144, vWF and CD34, CD45, CD14, GAPDH, expressed in endothelial cells. MOMCs before inducing differentiation and RNA derived from cultured umbilical vein endothelial cell (HUVEC) were used as control.

Example 8

Flow Cytometry Analysis

Fluorescent cell staining was performed with the following steps. The adherent cells were detached from the plastic plates by incubation with 2 mM EDTA on ice, and blocked with normal mouse or rat serum for 10 min at under 4° C. The cells were stained with the following mouse mAbs or rat anti-Sca-1 mAb (Cedarlane Laboratories), which were either unconjugated or conjugated to FITC, phycoerythrin (PE) or PC5: anti-HLA-DR antibody, anti CD11c antibody (BD Pharmingen), anti-CD11b/Mac-1 antibody, anti-CD14 antibody, anti-CD29 antibody, anti-CD34 antibody, anti-CD44 antibody, anti-CD83 antibody, anti-CD105/endoglin/SH2 antibody, anti-CD117/c-kit antibody (Immunotech), anti-CD34 antibody, anti-CD133 antibody (Miltenyi Biotech), anti-HLA class I antibody, anti-HLA-DR antibody, anti-CD31/PECAM-1 antibody, anti-Flt-1/VEGFR1 antibody, anti-Flk-1/VEGFR2 antibody (Sigma), anti-CD40 antibody, anti-CD54 antibody, anti-CD80 antibody, anti-CD86 antibody (Ancell), anti-CD144/VE-cadherin antibody, or anti-type I collagen antibody (Chemicon International). When unconjugated mAbs were used, goat anti-mouse antibody or rat IgG F (ab')$_2$ antibody conjugated to FITC or PE (Immunotech) was used as a secondary antibody. For intracellular staining, the cells were permeabilized and fixed by using IntraPrep™ permeabilization reagent (Immunotech). Cells were analyzed on a FACSCalibur flow cytometer (Becton Dickinson) by using the Cell Quest software. Visualized cells were identified by gating on forward and side scatters, and the data are shown as logarithmic histograms or dot-plots.

Example 9

Immunohistochemistry

Slides were coated with monocytes, macrophages, or dendritic cells by using a cytospin technique, and the remaining cell types were cultured on fibronectin-coated chamber slides, except for samples to be used for fibronectin staining, for which type I collagen-coated slides were used instead. The cells were fixed with 10% formalin, and the endogeneous peroxidase activity was suppressed with 3% peroxide for 5 min. Slides were incubated for 30 min with one of the following mouse mAbs, or rat anti-Sca-1 mAb: anti-CD45 antibody, anti-vimentin antibody, anti-skeletal muscle-specific actin antibody (SkM-actin) (Dako), anti-CD34 antibody (Calbiochem-Novabiochem), anti-type I collagen antibody (Chemicon), anti-type III collagen antibody, anti-fibronectin antibody (Sigma), anti-type II collagen antibody (ICN Biomedicals) or anti-skeletal muscle-specific myosin heavy chain antibody (SkM-MHC) (Zymed Laboratories). The slides were then further incubated with biotin-labeled anti-mouse antibody and anti-rat IgG antibody. The antibody-biotin conjugates were detected with a streptavidin-horseradish peroxidase complex (Nichirei) applied for 10 min at room temperature by using 3,3'-diaminobenzidine as the substrate. Nuclei were counterstained with hematoxylin. The negative controls were cells incubated with normal mouse- or rat-IgG antibody (DAKO) instead of the above-mentioned primary antibody.

Fluorescence double-staining was performed as follows. The cells were fixed with 4% paraformaldehyde, and incubated with goat anti-PEBP2αA antibody or anti-Sox9 polyclonal antibody (Santa Cruz), followed by incubation with AlexaFluor R568 goat-specific IgG antibody (Molecular Probes) and then with FITC-conjugated mouse anti-CD45 mAb (Dako). Similarly, the cells were stained with mouse anti-MyoD antibody (Dako) or anti-peroxisome proliferation-activated receptor γ (PPARγ gene) mAb (Santa Cruz), followed by incubation with tetramethylrhodamine isothiocyanate isomer R-labeled mouse-specific IgG antibody (Dako) and subsequently with FITC-conjugated anti-CD45 mAb. The cells were examined with a confocal laser fluorescence microscope (LSM5 PASCAL; Carl-Zeiss). To enumer-

Example 10

Uptake of Acetylated LDL (Ac-LDL)

The adherent cells were cultured with 2.5 μg/ml Dil-Ac-LDL (Molecular Probes) for 1 hour, and Ac-LDL uptake was evaluated by flow cytometry.

Example 11

Alkaline Phosphatase Staining

The cells were fixed with 10% formalin and subsequently incubated in a solution containing 0.2 mg/ml naphthol AS-TR phosphate and 0.5 mg/ml Fast Red RC (all from Sigma) for 10 min.

Example 12

Intracellular Calcium Detection

To evaluate intracellular calcium deposits, the cells were fixed with 10% formalin and stained with 2% alizarin red S (Sigma) for 3 min, followed by extensive wash with distilled water. The intracellular calcium concentration was measured by using a commercially available kit (Sigma) (J Biol Chem., 275, 9645-9652, 2000). The protein content in cell extract was also measured by using the Bradford protein assay kit (Bio-Rad Laboratories) by using bovine serum albumin as a standard. The calcium concentration was expressed as microgram per microgram of protein content.

Example 13

Oil-Red-O Staining

The cells were fixed with 0.2% glutaraldehyde for 5 min, washed with 60% isopropanol, and covered with 0.1% Oil-red-O (Sigma) for 10 min. After washing with 60% isopropanol and subsequently with distilled water, the cells were counterstained with hematoxylin.

Example 14

Transmission Electron Microscopy

Cultured MOMCs were immediately fixed with 2.5% glutaraldehyde, post-fixed with 2% osmium tetroxide, dehydrated in a series of ethanol and propylene oxide, and embedded in Epoxy resin. The cells were thin-sectioned on a LKB ultratome with a diamond knife. Sections in the range of gray to silver were collected on 150-mesh grids, double-stained with uranyl acetate and lead citrate, and examined under a JEOL-1200 EXII electron microscope (Jeol).

Example 15

Cell Proliferation Studies

Proliferating MOMCs were detected by BrdU-labeling as described previously (Blood, 71, 1201-1210, 1988). It is explained briefly in the following. MOMCs were cultured in the presence of 10 μM BrdU (Sigma) for 2 hours before staining. After a 30-minute fixation in Carnoy's fixative (methanol/acetic acid) at −20° C., the cells were air-dried, treated with 2N-HCl for 1 hour to denature DNA, and then neutralized with 0.1 M borate (pH 8.5) for 10 minutes. The cells were then incubated with mouse anti-BrdU mAb (Chemicon International), followed by biotin-streptavidin-peroxidase complex staining. Nuclei were counterstained with hematoxylin. Negative controls were the cells incubated with isotype-matched mouse control mAb instead of the above-mentioned primary antibody. Apoptotic cells were detected by incubating unfixed cells with propidium iodide (Sigma) for 30 min, and observed under a fluorescent microscope.

For cell-division studies, the cells were labeled with 5-carboxyfluorescein diacetate succinimidyl ester (CFSE) as described previously (J Exp Med., 183, 2313-2328, 1996). CFSE-labeled monocytes were cocultured with unlabeled $CD14^-$ cells on fibronectin-coated plated for 1, 3 and 5 days, and the adherent cells were harvested and stained with PC5-labeled anti-CD14 mAb. CFSE-labeled MOMCs were also cultured for 1, 3 and 5 days. The color intensity of CFSE labeling was evaluated by flow cytometry.

Example 16

RT-PCR

Total RNA was extracted from MOMCs that had or had not been induced to differentiate by using the RNeasy kit (Qiagen). Total RNA was also extracted from peripheral blood $CD14^+$ monocytes and macrophages, dendritic cells, dermal fibroblasts, myoblasts, and various cultured cells including osteosarcoma, rhabdomyosarcoma, and chondrosarcoma. Human muscle- and fat tissue-derived total RNAs were purchased from Clonetech Laboratories. Single-strand cDNA was synthesized from the total RNA by using Molony murine leukemia virus reverse transcriptase (Takara) with oligo-dT as a primer. The cDNA (equivalent to 50 ng total RNA) was then subjected to PCR amplification by using various specific primers listed in Table 1, shown by SEQ ID NOs: 3 to 34. The PCR products were resolved by electrophoresis on 2% agarose gels and visualized by staining with ethidium bromide.

TABLE 1

| Gene | Primer sequences | Product size (bp) |
|---|---|---|
| Osterix | Sense: 5'-CTTGTGCCTGATACCTGCACT-3' (SEQ ID NO: 3) Antisense: 5'-TCACTCTACCTGACCCGTCATC- 3' (SEQ ID NO: 4) | 470 |
| Bone sialoprotein | Sense: 5'-AAACGGCACCAGTACCAACA 3' (SEQ ID NO: 5) | 394 |

TABLE 1-continued

| Gene | Primer sequences | Product size (bp) |
|---|---|---|
| II | Antisense: 5'-GCCATCGTAGCCTTGTCCTT- 3'<br>(SEQ ID NO: 6) | |
| Osteocalcin | Sense: 5'-GGCAGCGAGGTAGTGAAGAGAC-3'<br>(SEQ ID NO: 7)<br>Antisense: 5'-GGCAAGGGGAAGAGGAAAGAAG-3'<br>(SEQ ID NO: 8) | 257 |
| SkM-MHC | Sense: 5'-ATAGGAACACCCAAGCCATC-3'<br>(SEQ ID NO: 9)<br>Antisense: 5'-TTTGCGTAGACCCTTGACAG- 3'<br>(SEQ ID NO: 10) | 599 |
| Myogenin | Sense: 5'-TGGCCTTCCCAGATGAAACC-3'<br>(SEQ ID NO: 11)<br>Antisense: 5'-GCATCGGGAAGAGACCAGAA-3'<br>(SEQ ID NO: 12) | 452 |
| α1 (II) collagen | Sense: 5'-TTCAGCTATGGAGATGACAATC-3'<br>(SEQ ID NO: 13)<br>Antisense: 5'-AGAGTCCTAGAGTGACTGAG- 3'<br>(SEQ ID NO: 14) | 472 |
| α1 (X) collagen | Sense: 5'-AATCCCTGGACCGGCTGGAATTC-3'<br>(SEQ ID NO: 15)<br>Antisense: 5'-TTGATGCCTGGCTGTCCTGGACC-3'<br>(SEQ ID NO: 16) | 267 |
| PPARγ | Sense: 5'-AGGAGCAGAGCAAAGAGGTG- 3'<br>(SEQ ID NO: 17)<br>Antisense:5'-AGGACTCAGGGTGGTTCAGC-3'<br>(SEQ ID NO: 18) | 474 |
| aP2 | Sense: 5'-TATGAAAGAAGTAGGAGTGGGC-3'<br>(SEQ ID NO: 19)<br>Antisense: 5'-CCACCACCAGTTTATCATCCTC-3'<br>(SEQ ID NO: 20) | 290 |
| CD34 | Sense: 5'-CCTCCCAAGTTTTAGGACAA-3'<br>(SEQ ID NO: 21)<br>Antisense: 5'-CAGCTGGTGATAAGGGTTAG-3'<br>(SEQ ID NO: 22) | 362 |
| CD45 | Sense: 5'-AACCTGAAGTGATGATTGCTG- 3'<br>(SEQ ID NO: 23)<br>Antisense: 5'-TACCTCTTCTGTTTCCGCAC-3'<br>(SEQ ID NO: 24) | 500 |
| CD14 | Sense: 5'-CTGCGTGTGCTAGCGTACTC-3'<br>(SEQ ID NO: 25)<br>Antisense: 5'-CGTCCAGTGTCAGGTTATCC-3'<br>(SEQ ID NO: 26) | 655 |
| Cbfa1/Runx2 | Sense: 5'-GTCTTACCCCTCCTACCTGA-3'<br>(SEQ ID NO: 27)<br>Antisense: 5'-TGCCTGGCTCTTCTTACTGA- 5'<br>(SEQ ID NO: 28) | 183 |
| MyoD | Sense: 5'-CCTAGACTACCTGTCCAGCATC- 3'<br>(SEQ ID NO: 29)<br>Antisense: 5'-GGCGGAAACTTCAGTTCTCC-3'<br>(SEQ ID NO: 30) | 365 |
| Sox-9 | Sense: 5'-CCCGATCTGAAGAAGGAGAGC-3'<br>(SEQ ID NO: 31)<br>Antisense: 5'-GTTCTTCACCGACTTCCTCCG- 3'<br>(SEQ ID NO: 32) | 380 |
| GAPDH | Sense: 5'-TGAACGGGAAGCTCACTGG-3'<br>(SEQ ID NO: 33)<br>Antisense: 5'-TCCACCACCCTGTTGCTGTA-3'<br>(SEQ ID NO: 34) | 307 |

Example 17

Statistical Analysis

All comparisons were tested for statistical significance by using Mann-Whitney U test.

RESULTS

Example 18

Generation of MOMCs

Figure 2:
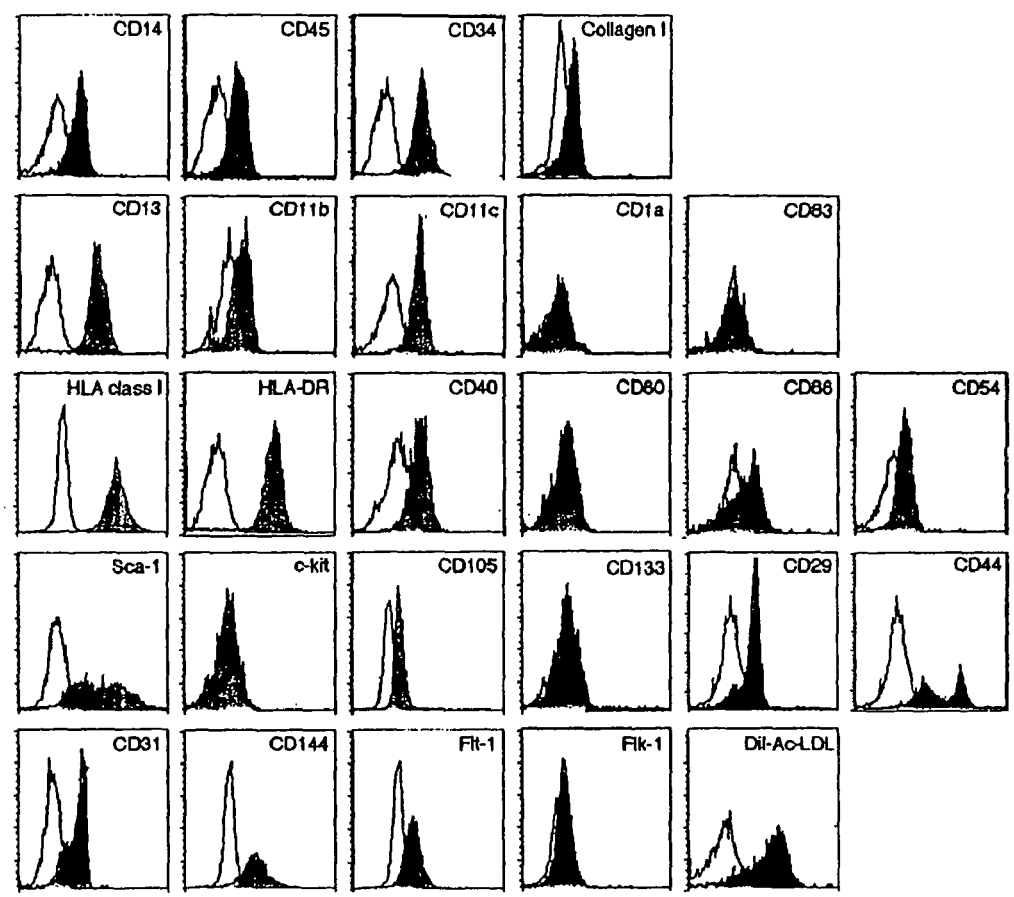
FIG. 2 shows the result of flow cytometric analysis of MOMCs of the present invention. PMBCs were cultured on fibronectin-coated plates and the adherent cells were harvested on Day 7. The cells were stained with a series of mAbs shown in the picture and analyzed by flow cytometry. The expression of the molecule of interest is shown as shaded histograms. Open histograms represent controls stained with isotype-matched control mAbs. The results shown are representative of at least three experiments.

When PBMCs were cultured on fibronectin-coated plates in DMEM supplemented only with 10% FBS, a subset of cells immediately attached to the plates. Small clusters of round cells developed within 24 hours, and cell processes extended from them. After 5 days of culture, adherent cells with a fibroblast-like morphology made their appearance. Over the ensuing 3 days, the fibroblast-like cells became the predominant cell type in the culture (FIG. 1a). The fibroblast-like cells were frequently detected around the clusters (FIG. 1b). The number of fibroblast-like cells increased slowly until around Day 14. After this time, the proliferating ability gradually stopped but the cells survived for up to 4 weeks. When $10^8$ PBMCs obtained from 50 donors were cultured, 0.3 to 1.0× $10^7$ adherent cells were obtained at Day 7. From flow cytometric analysis, the cells harvested on Day 7 showed to comprise a single phenotype (95% or more were homogeneous) and to be positive for CD14, CD45, CD34, and type I collagen (FIG. 2). This phenotype is unique and distinct from that of known adherent cells of peripheral blood origin, including monocytes/macrophages ($CD14^+$, $CD45^+$, $CD34^-$ and type I collagen$^-$), endothelial progenitors ($CD14^-$, $CD45^-$, $CD34^+$ and type I collagen$^-$) (Science, 275, 964-967, 1997), and mesenchymal progenitors ($CD14^-$, $CD45^-$, $CD34^-$, type I collagen$^+$) (Arthritis Res., 2, 477-488, 2000). Cells obtained from at least 50 donors showed the same phenotype. After the cells were moved on new fibronectin-coated plates on Day 7 and cultured under the same conditions, nearly all the cells adopted an elongated fibroblast-like morphology (FIG. 1c). These cells could be expanded up to 5 passages, and the cell proliferation was likely to be most active just after the passage. However, after 5 passages, the cell proliferation speed became gradually slow, and the proliferation ability disappeared after 8 passages. The cells did not differentiate naturally into mature mesenchymal cells during the culture when no particular treatment was performed. However, when cells were inoculated at a high confluency, cells with plural nuclei appeared at a very low frequency. These fibroblast-like cells obtained from PBMCs from a culture in vitro, were named MOMC from the following findings.

By electron microscopic examination, it was revealed that MOMCs had a spindle shaped morphology and contained a number of cytoplasmic organelles (FIGS. 1d-g). Multiple primary lysosomes, cell surface projections like pseudopodia, and labyrinth-like endocytic vesicles are specific observations that are also found in macrophages and other phagocytes. MOMCs also had prominent bundles of intermediate filaments, well-developed secondary lysosomes, and elongated and branching mitochondria, which are characteristics frequently seen in cells of mesenchymal origin. Small lipid droplets were observed in almost all MOMCs. In addition, structures similar to rod-shaped micro-tubulated bodies, which are specific to endothelial cells, were frequently detected. These ultrastructural findings represented mixed features of phagocytes, and mesenchymal and endothelial cells.

Example 19

Origin of MOMCs in Circulation

The adherent cells obtained in the PBMC culture on fibronectin-coated plates were serially examined for their surface expression of CD14 and CD34 by flow cytometry (FIG. 3a). The majority of cells attached to the plates at 1 hour were $CD14^+$ and $CD34^-$, but CD34 expression gradually up-regulated on the adherent $CD14^+$ cells. Nearly all the adherent cells were positive for both CD14 and CD34 after 7 days in culture. As peripheral blood contained $CD34^+$ endothelial progenitors (Science, 275, 964-967, 1997) and CD105/endoglin/$SH2^+$ mesenchymal progenitors (Science, 284, 143-147, 1999; Arthritis Res., 2, 477-488, 2000; Biochem Biophys Res Commun., 265, 134-139, 1999), the present inventors examined the effect of depleting PBMCs of cells positive for CD14, CD34, or CD105 on the in vitro induction of MOMCs. As shown in FIG. 3b, the appearance of MOMCs was almost completely inhibited by the depletion of $CD14^+$ monocytes, whereas depletion of $CD34^+$ or $CD105^+$ cells showed no effect. To further confirm that MOMCs originated from circulating monocytes, $CD14^+$ monocytes were isolated from PBMCs, labeled with PKH67 and cultured with unlabeled $CD14^-$ cells on fibronectin-coated plates. As shown in FIG. 3c, PKH67-labeled monocytes expressed CD34 after one week of the culture. Together, these findings indicate that MOMCs originates from circulating $CD14^+$ monocytes. However, non-adherent cells collected on Day 3 contained a significant proportion of $CD14^+$ cells, which suggests that a subset of $CD14^+$ monocytes can attach to fibronectin and differentiate into MOMCs.

When PKH67-labeled monocytes were cultured alone on fibronectin, only a few cells became fibroblast-like and CD34 expression was not up-regulated at Day 7 (FIG. 3c). In this case, it was sufficient to add culture supernatant of $CD14^-$ cells to induce CD34 expression in monocytes. Furthermore, when coculturing $CD14^-$ cells with PKH67-labeled monocytes on plates that are not coated with fibronectin, the number of cells attached to the plates on Day 7 was low, and these adherent cells did not express CD34 (FIG. 3c). From these results, it is likely that the differentiation from circulating monocytes into MOMCs requires soluble factor (1 or more) derived from $CD14^-$ cells in peripheral blood and binding to fibronectin.

To evaluate whether $CD14^+$ monocytes proliferate during MOMC differentiation, $CD14^+$ monocytes were labeled with CFSE and cocultured with unlabeled $CD14^-$ cells on fibronectin. Adherent cells were serially harvested and examined for color intensity of CFSE labeling and CD14 expression by flow cytometry (FIG. 3d). Nearly all fibronectin-attached monocytes proliferated mainly during the first 24 hours of culture, and proliferated slowly later in culture. Adherent cells were almost exclusively CFSE-labeled $CD14^+$ monocytes, and the expansion of adherent cells from the $CD14^-$ cell fraction was not observed, suggesting that generation of MOMCs did not occur as a result from the growth of specific precursors in the mixed CD14⁻ cell population.

Example 20

Phenotype of MOMCs

Figure 4:
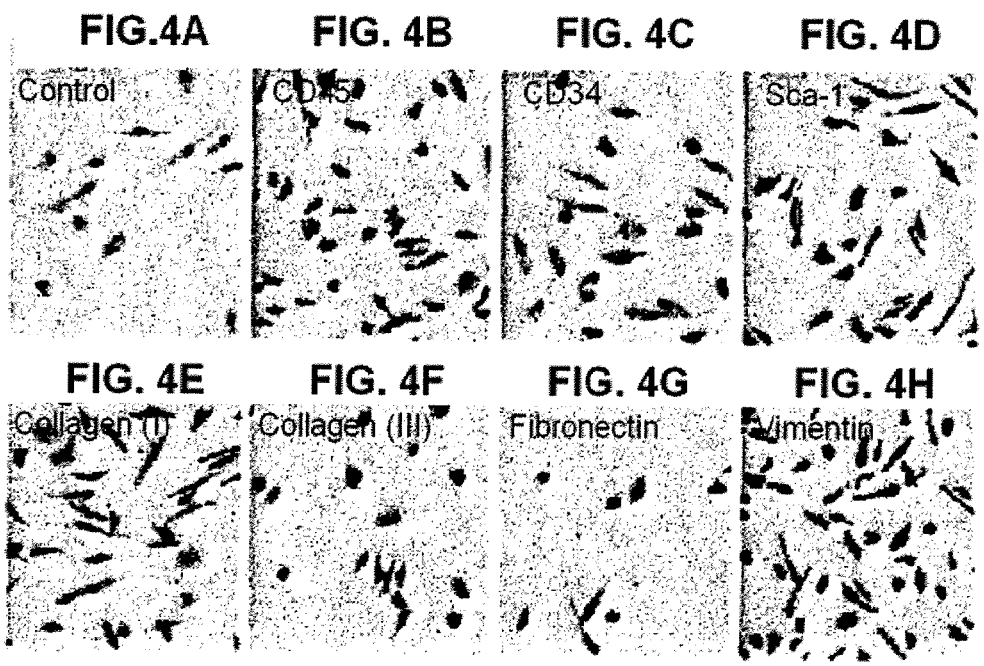
FIGS. 4A-H show the result of immunohistochemical analysis of MOMCs of the present invention. MOMCs generated by culturing PBMCs on fibronectin-coated plates for 7 days were moved onto fibronectin-coated chamber slides (The slides coated with type I collagen were only used for fibronectin staining). After 24 hours of culture, the above-mentioned slides were fixed with 10% formalin and stained with mAbs as indicated in the picture. The nuclei were counterstained with hematoxylin. Original magnification is ×100. The results shown are representative of at least three independent experiments.

Expression of various cell surface molecules and intracellular molecules of MOMCs was examined by flow cytometry and immunohistochemistry (FIGS. 2 and 4), and compared the protein expression profile with that of monocytes, macrophages, and dendritic cells (Table 2). MOMCs expressed hematopoietic and monocyte lineage marker genes (CD45, CD14, CD13, CD11b, CD11c, and CD64), but did not express dendritic cell marker genes (CD1a and CD83). The expression of HLA Class I, HLA-DR, and costimulatory molecules (CD40 and CD86) on MOMCs strongly suggests that MOMCs have an ability to induce antigen-specific T cell activation as antigen-presenting cells. MOMCs expressed hematopoietic stem/endothelial cell marker gene CD34, and mesenchymal stem/endothelial cell marker gene CD105/endoglin/SH2 (Biochem Biophys Res Commun., 265, 134-139, 1999). Moreover, MOMCs expressed stem cell marker gene Sca-1, but did not expressed different stem cell marker genes CD117/c-kit and CD 133. Further, MOMCs were positive for the endothelial marker gene CD144/VE-cadherin and Flt-1/VEGFR1, while Flk-1/VEFR2 and vWF expressions were not observed. MOMCs were also positive for type I and III collagen, fibronectin, and vimentin, which are extracellular matrix proteins typically produced by cells of mesenchymal origin. These protein expression profiles did not change for up to 5 passages. MOMCs showed distinct phenotypes from that of monocytes and monocyte-derived phagocytes. In particular, the expression of stem cell marker genes (CD34, Sca-1 and CD105), endothelial marker genes (CD144/VE-cadherin and Flt-1/VEGFR1), and mesenchymal marker genes (type I and III collagen, and fibronectin) is unique characteristic of MOMCs. Therefore, it can be recognized that MOMCs are cells with phenotypes of phagocytes, endothelial cells, mesenchymal cells and stem cells.

TABLE 2

|  | Monocytes | Macrophages | Dendritic cells | MOMCs |
|---|---|---|---|---|
| CD45 | ++ | ++ | + | + |
| Monocyte markers | | | | |
| CD14 | ++ | ++ | − | ++ |
| CD13 | + | + | + | ++ |
| CD11b/Mac-1 | ++ | + | ++ | + |
| CD11c | + | + | + | + |
| CD64 | + | + | − | + |
| Dendritic cell markers | | | | |
| CD1a | − | − | −/++[A] | − |
| CD83 | − | − | ++ | − |
| HLA molecules | | | | |
| HLA class I | ++ | +++ | +++ | ++ |
| HLA-DR | ++ | ++ | ++ | ++ |
| Costimulatory molecules | | | | |
| CD40 | + | + | ++ | + |
| CD80 | − | ++ | ++ | − |
| CD86 | + | + | +++ | + |
| Adhesion molecules | | | | |
| CD29 | + | + | + | + |
| CD44 | ++ | ++ | ++ | +/++[A] |

TABLE 2-continued

|  | Monocytes | Macrophages | Dendritic cells | MOMCs |
|---|---|---|---|---|
| CD54 | + | + | ++ | + |
| Stem cell/progenitor markers | | | | |
| CD34 | − | − | − | + |
| CD105/endoglin/SH2 | − | − | − | + |
| CD117/c-kit | − | − | − | − |
| CD133 | − | − | − | − |
| Sca-1 | − | − | − | +/++[A] |
| Endothelial cell markers | | | | |
| CD31 | + | + | + | + |
| CD144/VE-cadherin | − | − | − | + |
| Flt-1/VEGFR1 | − | − | − | + |
| Flk-1/VEFR2 | − | − | − | − |
| vWF[A] | − | − | − | − |
| Ac-LDL | + | ++ | − | ++ |
| Mesenchymal cell markers | | | | |
| Type I collagen | − | − | − | + |
| Type III collagen | − | − | − | + |
| Fibronectin | − | − | − | + |
| Vimentin | + | + | + | ++ |

Example 21

Proliferating Ability of MOMCs

MOMCs seemed to increase during culture. To investigate whether this observation is due to cell division, the proportion of dividing cells in MOMCs was evaluated serially by BrdU staining (FIG. 5a). Nearly half of the adherent cells were stained with BrdU after 1 day from the passage, but the number of cells of BrdU⁺ cells decreased significantly at Day 5. The proportion of BrdU⁺ cells to all adherent cells were calculated at Day 1, 3, 5, 7 and 10, and the proportion of BrdU⁺ cells were at the maximum at Day 1 during culture, and decreased chronologically afterwards. Cells positive for propidium iodide staining were less than 1% at all time points. By investigating using CFSE labeling, it appeared that MOMCs divided actively and synchronously after the passage and no subset of the cells proliferated predominantly (FIG. 5c). These findings suggest that MOMCs have proliferating ability during culture, and that mainly proliferate just after the passage.

Example 22

In Vitro Differentiation of MOMCs into Mesenchymal Cell Lineages

As MOMCs had some morphologic and phenotypic properties of mesenchymal cells, the present inventors hypothesized that MOMCs can be induced to differentiate into some mesenchymal lineages. To confirm this hypothesis, MOMCs were cultured under various conditions known to induce differentiation of MSCs into bone, skeletal muscle, cartilage and fat.

Figure 6:
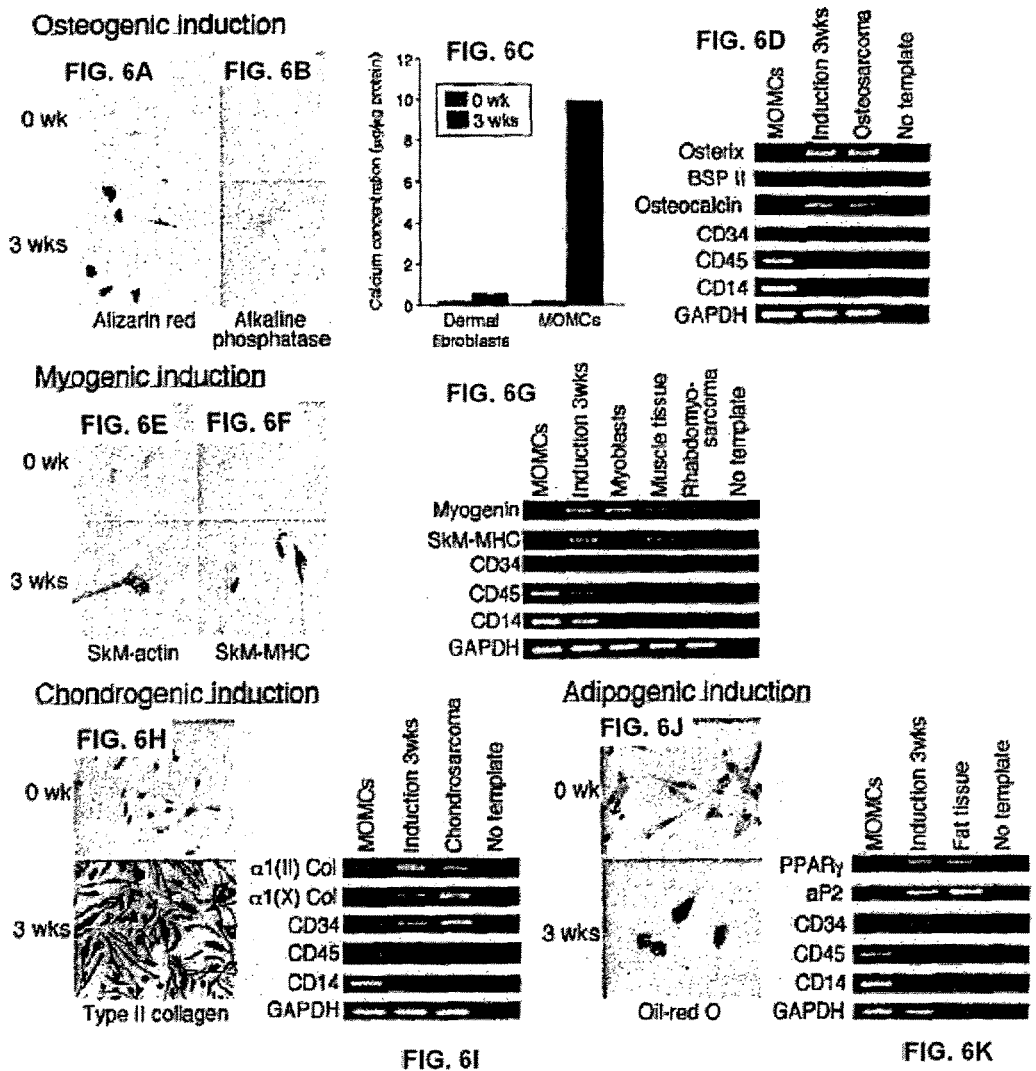
FIGS. 6A-K show osteogenic, myogenic, chondrogenic, and adipogenic differentiation of MOMCs of the present invention. MOMCs before and after three weeks of osteogenic induction were stained with Alizarin red (FIG. 6A; magnification ×100) or with alkaline phosphatase (FIG. 6B; ×100). The intracellular calcium deposition was measured in MOMCs and fibroblasts before and after osteogenic induction and expressed as microgram per microgram protein content (FIG. 6C). Expression of mRNAs for osterix, bone sialoprotein II (BSP II), osteocalcin, CD34, CD45, CD14 and GAPDH were examined in MOMCs before and after 3 weeks of osteogenic induction and in osteosarcoma cell line (FIG. 6D). MOMCs before and after 3 weeks of myogenic induction were stained, and SkM-actin staining (FIG. 6E; ×200) or SkM-MHC staining (FIG. 6F; ×200) were examined. Expression of mRNAs for myogenin, SkM-MHC, CD34, CD45, CD14, and GAPDH was examined in MOMCs before and after 3 weeks of myogenic induction and in myoblast, muscle tissue, and in rhabdomyosarcoma cell line (FIG. 6G). MOMCs before and after 3 weeks of chondrogenic induction were stained and type II collagen staining were examined (FIG. 6H; ×40). Expression of mRNAs for α1 (type II) and α1 (type X) collagen, CD34, CD45, CD14, and GAPDH was examined in MOMCs before and after 3 weeks of chondrogenic induction and in a chondrosarcoma cell line (FIG. 6I). MOMCs before and after 3 weeks of adipogenic induction were stained with Oil-red-O (FIG. 6J; ×200). Expression of the mRNAs for PPARγ, aP2, CD34, Cd45, CD14 and GAPDH was examined in MOMCs before and after three weeks of adipogenic induction and in fat tissue (FIG. 6K). The results shown are representative of at least five experiments.

MOMCs treated with the osteogenic induction procedure underwent a change in their morphology from spindle-shaped to cylinder-like form. It was observed that almost every adherent cell formed calcium deposits, by alizarin red staining (FIG. 6a), and these adherent cells expressed alkaline phosphatase (FIG. 6b). The intracellular calcium content was significantly increased during this process (FIG. 6c). After osteogenic induction, MOMCs expressed mRNAs for bone sialoprotein II produced by mature osteocytes and osteocalcin (Calcif Tissue Int. 62, 74-82, 1998) and for bone-specific transcription factor osterix (Cell, 108, 17-29, 2002). On the other hand, CD34, CD45, and CD14 expression was lost after this induction treatment (FIG. 6d).

When MOMCs were treated with 5-azacytidine and cultured under a condition inducing differentiation into muscle for 3 weeks, the cells became elongated, but no cells like myocytes with plural nuclei appeared. At this time point, expression of SkM-actin and SkM-MHC was induced in 45-60% of the adherent cells, depending on the sample (FIGS. 6e and 6f). By RT-PCR, mRNAs for the muscle-specific transcription factor myogenin and SkM-MHC were detected after induction (FIG. 6g). The expression of CD34, CD14, and CD45 was reduced but not lost. Immunohistochemical analysis revealed that CD34 was expressed in nearly all adherent cells, but CD14 and CD45 were expressed in cells that did not express SkM-MHC (data not shown). The expression CD34 was also detectable in cultured myoblasts and muscle tissue, and even in a rhabdomyosarcoma cell line, consistent with the expression of CD34 in a subset of primitive muscle cells (J Cell Biol., 150, 1085-1100, 2000).

To induce cartilage formation, MOMCs were cultured in micromass suspension in the presence of TGF-β1, which is a standard method to induce chondrocyte differentiation in MSC (Science, 284, 143-147, 1999; Tissue Eng., 4, 415-428, 1998; Arthritis Rheum., 44, 85-95, 2001). However, MOMCs died within 1 week even in culture according to several different protocols by droplet-micromass on plates, or pelette-macromass in conical tube. Therefore, monolayer MOMCs were cultured in the presence of TGF-β1 for 3 weeks. As it is shown in FIG. 6h, type II collagen typical of articular cartilage, was weakly expressed in untreated MOMCs, but its expression was markedly up-regulated after induction treatment. Results of RT-PCR further demonstrated the up-regulated expression of chondrocyte-specific type II and type X collagen after the induction treatment (FIG. 6i). The expression of CD45 and CD14 was lost, but CD34 expression was retained after the induction treatment. On the other hand, CD34 was also expressed in a chondrosarcoma cell line.

Electron microscopic examination revealed small lipid droplets in MOMCs (FIGS. 1d, f and g). After the induction treatment, lipid vacuoles appeared and increased over time in both size and number. These lipid vacuoles were stained with Oil-red-O (FIG. 6j). From this induction treatment, 50 to 80% of the adherent cells were committed to this lineage, depending on the sample. mRNAs for PPARγ genes, and mRNAs for the fatty acid binding protein aP2 were weakly expressed in MOMCs, but the expression of these genes were markedly up-regulated after the above-mentioned induction treatment (FIG. 6k). Expression of mRNAs for CD45 and CD14 was lost, but CD34 expression was retained after the induction treatment. On the other hand, CD34 was also expressed in fat tissues.

The differentiation into mesenchymal cells was observed in MOMCs that were freshly generated from PBMCs, cultured for up to five passages or cryo-preserved. In addition, MOMCs obtained from 5 donors showed similar differentiation potential. Two strains of human dermal fibroblasts, which are mature mesenchymal cells as well as freshly isolated CD14$^+$ monocytes and macrophages, were also cultured under the identical induction conditions. After 3 weeks, the dermal fibroblasts did not show any differentiation tendency in these conditions, although the cells appeared healthy. After 1 week, circulating monocytes and macrophages subjected to these culture conditions detached from the plates without apparent differentiation. Lineage-specific differentiation was observed in more than half of the adherent cells after 3 weeks of culture. But the number of the adherent cells decreased for 20 to 50% from the initial number of cells, suggesting that most MOMCs were detached during the induction process.

To investigate whether the differentiation into a certain lineage is specific to various induction treatments, cultures from each treatment were cross-stained with alizarin red, Oil-red-O, and were also immunostained with SkM-MHC or type II collagen. These cells were positive only for the staining specific to the intended lineage, and negative to all other stainings (data not shown). Furthermore, to investigate the possibility that some subsets differentiate into lineage other than the intended lineage in an in vitro assay, cells treated with differentiation induction for 3 weeks were subjected to high-sensitive RT-PCR, to amplify the transcripts of plural genes wherein the expression is limited to osteogenic (osteocalcin), myogenic (SkM-MHC), chondrogenic (type II collagen), or adipogenic (aP2) lineage. Expression of lineage-specific gene was specific to the intended lineage (data not shown), suggesting that the differentiation was exhibited specifically to the performed treatment.

Figure 7:
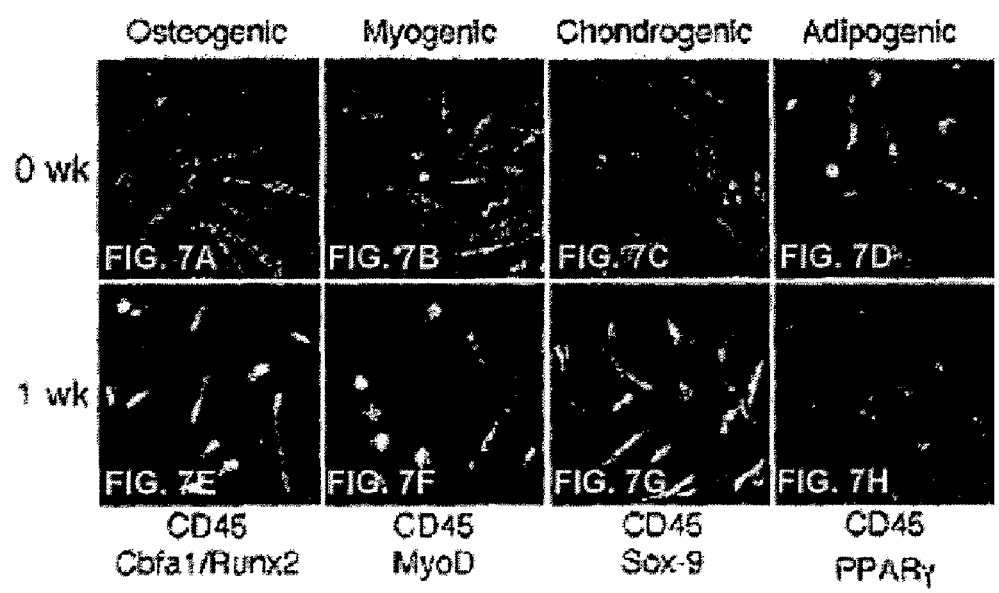
FIGS. 7A-H show the coexpression of CD45 (green) and tissue-specific transcription factors (red) in MOMCs of the present invention that underwent 1 week of mesenchymal differentiation. MOMCs before induction treatment (FIGS. 7A-D) and MOMCs treated for osteogenic FIG. 7E, myogenic FIG. 7F, chondrogenic FIG. 7G or adipogenic FIG. 7H induction for 1 week were examined for the immunohistochemical localization of CD45 in combination with Cbfa1/Runx2 (FIG. 7A and FIG. 7E), MyoD (FIG. 7B and FIG. 7F), Sox-9 (FIG. 7C and FIG. 7G), or PPARγ (FIG. 7D and FIG. 7H). The cells were observed with confocal laser fluorescence microscopy (original magnification ×200). The results shown are representative of three experiments.

To exclude the possibility that the differentiated mesenchymal cells were derived from cells with differentiation potential as MSC contaminated into MOMC fractions, CD14$^+$ cells were positively purified from the MOMCs by using the MACS separation system before the induction treatment. As expected, the differentiation into the osteogenesis, myogenesis, chondrogenesis, and adipogenesis was observed as for the unselected MOMCs. In addition, the depletion of cells expressing CD34 or CD105/endoglin/SH2 at the initiation of PBMC cultures did not affect the differentiation into mesenchymal cells. Further the expression of lineage-specific transcription factors, Cbfa1/Runx2 (Cell, 89, 755-764, 1997), MyoD (Front Biosci., 5, D750-767, 2000), Sox-9 (Osteoarthritis Cartilage, 8, 309-334, 2000), and PPARγ (J Biol Chem., 276, 37731-37734, 2001), in MOMCs after 1 week of induction treatment, was examined. As at this time point, as MOMCs were expressing CD45, MOMCs that underwent osteogenic, myogenic, chondrogenic, or adipogenic induction treatment were double-stained, to investigate the expression of CD45 and individual transcription factors. As shown in FIG. 7, MOMCs that underwent osteogenic differentiation for 1 week, expressed CD45 in cell membrane and cytoplasma, and Cbfa1/Runx2 in nucleus. Similarly, simultaneous expression of CD45/MyoD and CD45/Sox-9 was observed in MOMCs that underwent induction of myogenic and chondrogenic differentiation for 1 week. PPARγ was weakly expressed in the nuclei of untreated MOMCs, but after 1 week of adipogenic induction, the PPARγ expression increased and the CD45 expression decreased. These findings suggest that CD45$^+$ hemapoietic cells underwent lineage-specific differentiation under specific conditions inducing differentiation. The expression of these lineage-specific transcription factors, except PPARγ, was lost at 3 weeks of the induction treatment as determined by immunohistochemistry and RT-PCR (data not shown). These findings suggest that MOMCs express transiently the above-mentioned lineage-

Example 23

In Vitro Differentiation of MOMCs into Myocardial Cells

Nestin (brown), a marker expressing in nerve and myocardial progenitors, was expressed in MOMCs at Day 8 of coculture, and binding with surrounding rat-cultured myocardial cells was observed (FIG. 8A).

MOMCs labeled with PKH67 (Green) expressed myocardial cell-specific transcription factors Nkx2.5, eHAND (Red/Alexa568: Molecular Probe), and expressed simultaneously CD45, a hematopoietic marker (Blue/Alexa660: Molecular Probe) (FIGS. 8B, C). This shows the differentiating process of MOMCs derived from human peripheral blood hemocyte into myocardial cells.

By RT-PCR using human-specific PCR primer, expression of myocin light chain (MLC2v) which is a myocardial cell structural protein was observed in human cardiac muscle, the positive control, while no expression was observed in rat-cardiac muscle, the negative control, nor in MOMCs before coculture. In MOMCs at Day 12 of coculture, expression of human MLC2v was observed (FIG. 8D).

From these results, with the coculture of MOMCs with rat-myocardial cells, induction of differentiation of MOMCs into myocardial cells was demonstrated, as well as the expression of myocardial progenitor marker at Day 8-10 of coculture, and the expression of myocardial structural protein at Day 12-14.

Example 24

In Vitro Differentiation of MOMCs into Neurons

Figure 9:
FIGS. 9A-E show how MOMCs of the present invention differentiate into neurons. Nestins (brown), which are markers expressing in nerve/myocardial progenitors, and being expressed in MOMCs cocultured with Wistar rat-cultured neurons for 8 days were immunostained (FIG. 9A ×200). After labeling cell membrane with fluorescent PKH67 (green), MOMCs were cocultured with Wistar rat-cultured neurons for 4 days, and were double fluorescently immunostained with NeuroD (red), a neuron-specific transcription factor, and CD45 (blue), a hematopoietic marker (FIG. 9B ×200). MOMCs were cocultured with Wistar rat-cultured neurons for 3 days, and were double fluorescently immunostained with nestin (brown) and Neurogenin 2 (red), a neuron-specific transcription factor (FIG. 9C ×200). PKH67-labeled MOMCs (green) were cocultured with Wistar rat-cultured neuron for 3 days, and were double fluorescently immunostained with Hu (red), a mature-nerve marker (FIG. 9D ×200). PKH67-labeled MOMCs were cocultured with Wistar rat-cultured neuron for 9 days, and were fluorescently immunostained with NeuN (red), a mature-nerve marker (FIG. 9E ×200). The results shown are representative of three experiments.
Figure 9:
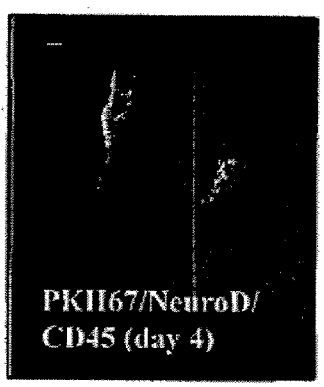
Figure 9:
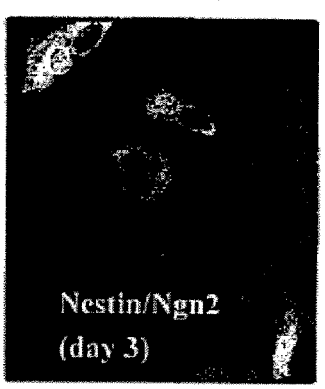
Figure 9:
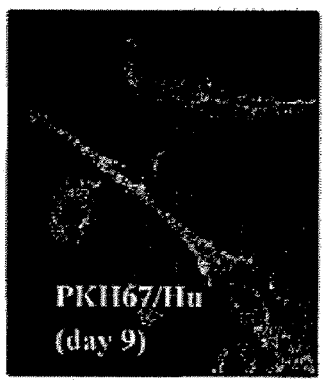
Figure 9:
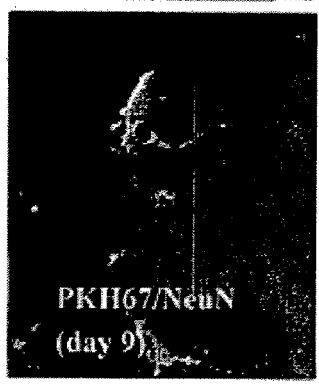

Nestin (brown), a marker expressing in nerve and myocardial progenitors, was expressed in MOMCs at Day 8 of coculture, and elongation of nerve projection toward surrounding rat-cultured neurons was observed (FIG. 9A).

MOMCs labeled with PKH67 (Green) expressed a neuron-specific transcription factor NeuroD (Red/Alexa568: Molecular Probe) at Day 4 of coculture, and expressed simultaneously CD45 a hematopoietic marker (Blue/Alexa660: Molecular Probe) (FIG. 9B). This shows the differentiating process of MOMCs derived from human peripheral blood hematopoietic cells into neurons.

At Day 3 of coculture, at the same time MOMCs expressed nestin (Green/Alexa488: Molecular Probe), Neurogenin2 (red/Alexa568: Molecular Probe), which is a neuron-specific transcription factor was expressed (FIG. 9C). From these results, MOMCs were shown to be a progenitor of neurons, whose differentiation into neuron is determined.

With 9 days of coculture with Wistar rat-cultured neuron, expression of mature nerve markers Hu, NeuN (Red/Alexa568: Molecular Probe) was observed (FIGS. 9D, and E) in MOMCs labeled with PKH67 (Green). These results demonstrated that MOMCs differentiate up to mature neurons.

Example 25

In Vitro Differentiation of MOMCs into Endothelial Cells

MOMCs that underwent induction of differentiation in EBM-2 medium for 7 days, changed their morphology from spindle shape to a morphology having multiple projections, and expressed vWF, eNOS, VEGFR2/KDR/Flk-1 specific to endothelial cells that were not expressed originally.

From a gene expression analysis by RT-PCR, in MOMCs that underwent induction of differentiation in EMB-2 medium for 7 days, expression of genes Flt-1, VEGFR2/KDR/Flk-1, CD31, CD144, vWf characteristic to endothelium was observed. Expression of Flt-1 and CD31 was observed in MOMCs, but other genes were expressed after the induction. After inducing differentiation, CD34 expression was enhanced, and expression of CD45, CD 14 was lost.

From these results, it was demonstrated that by culturing MOMCs in maintenance medium of endothelial cells, differentiation into endothelial cells was induced.

INDUSTRIAL APPLICABILITY

According to the present invention, a monocyte-derived multipotent cell, MOMC, having a potential to differentiate into various cells such as mesenchymal cells including bone, cartilage, skeletal muscle and fat, endothelial cells, myocardial cells, neurons, very useful to cell therapy or regenerative medicine can be obtained. Moreover, as monocytes can be easily obtained without much invasion from peripheral blood, and monocytes represent about 20% of the peripheral blood mononuclear cells, sufficient cells necessary can be supplied in a stable manner. Inducing differentiation from monocytes into MOMCs can be performed easily, rapidly at a low cost, and no particular device is needed. Further, as autologous cells can be used for cell transplantation, there are no problems such as securing donors, or rejection symptoms, and fewer ethical problems. The present invention challenges the traditional and biological view regarding the monocyte/phagocyte systems and will contribute greatly to the understanding of the differentiation potential of monocytes and the roles they play for retaining homeostatis of the living body and induction of pathology.

---

The invention claimed is:

1. An isolated monocyte-derived multipotent cell (MOMC) expressing CD14, CD34, CD45, type I collagen, and HLA-DR, wherein the cell differentiates into osteoblasts, skeletal myoblasts or chondrocytes, and the monocyte-derived multipotent cell (MOMC) is obtained by culturing peripheral blood mononuclear cells (PBMCs) in vitro on fibronectin, and collecting fibroblast-like cells expressing CD14 and CD34.

2. The isolated monocyte-derived multipotent cell (MOMC) according to claim 1, that differentiates into mesenchymal cells by a culture under a condition inducing differentiation into mesenchymal tissues.

3. The isolated monocyte-derived multipotent cell (MOMC) according to claim 2, wherein the mesenchymal cells are adipocytes.

4. The isolated monocyte-derived multipotent cell (MOMC) according to claim 1, that differentiates into myocardial cells by a coculture with cultured myocardial cells.

5. The isolated monocyte-derived multipotent cell (MOMC) according to claim 1, that differentiates into neurons by a coculture with cultured neurons.

6. The isolated monocyte-derived multipotent cell (MOMC) according to claim 1, that differentiates into endothelial cells by a culture under a condition maintaining endothelial cells.

7. The isolated monocyte-derived multipotent cell (MOMC) according to claim 1, that differentiates into mesodermal cells.

8. A method for preparing the monocyte-derived multipotent cell according to claim 1, comprising culturing peripheral blood mononuclear cells (PBMCs) in vitro on fibronectin, and collecting fibroblast-like cells expressing CD14, CD34, CD45, type I collagen, and HLA-DR.

9. The method for preparing the monocyte-derived multipotent cell according to claim 8, comprising culturing in vitro on fibronectin for 5 to 14 days.

* * * * *